United States Patent
Higashi et al.

(10) Patent No.: US 11,992,320 B2
(45) Date of Patent: May 28, 2024

(54) SENSOR AND INSPECTION DEVICE

(71) Applicant: KABUSHIKI KAISHA TOSHIBA, Tokyo (JP)

(72) Inventors: Yoshihiro Higashi, Komatsu Ishikawa (JP); Akira Kikitsu, Yokohama Kanagawa (JP); Satoshi Shirotori, Yokohama Kanagawa (JP); Yoshinari Kurosaki, Kawasaki Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 145 days.

(21) Appl. No.: 17/682,998

(22) Filed: Feb. 28, 2022

(65) Prior Publication Data
US 2023/0074881 A1    Mar. 9, 2023

(30) Foreign Application Priority Data

Sep. 7, 2021   (JP) .................. 2021-145587

(51) Int. Cl.
*G01R 33/09*   (2006.01)
*A61B 5/245*   (2021.01)

(52) U.S. Cl.
CPC ............ *A61B 5/245* (2021.01); *G01R 33/093* (2013.01); *A61B 2562/0223* (2013.01); *A61B 2562/046* (2013.01)

(58) Field of Classification Search
CPC ................................. G01R 33/093
See application file for complete search history.

(56) References Cited

U.S. PATENT DOCUMENTS

| | | | |
|---|---|---|---|
| 2015/0192432 A1* | 7/2015 | Noguchi | G01D 5/145 324/207.2 |
| 2018/0003776 A1* | 1/2018 | Suess | G01R 33/098 |
| 2018/0271395 A1* | 9/2018 | Iwasaki | A61B 5/24 |
| 2019/0369172 A1 | 12/2019 | Kikitsu et al. | |

(Continued)

FOREIGN PATENT DOCUMENTS

| | | |
|---|---|---|
| JP | 2007-240289 A | 9/2007 |
| JP | 2018-155719 A | 10/2018 |

(Continued)

OTHER PUBLICATIONS

A. Guedes et al., "Hybrid GMR Sensor Detecting 950 pTsqrt(Hz) at 1 Hz and Room Temperature," Sensors 18, No. 3, 790, 8 pages (2018).

(Continued)

*Primary Examiner* — Alesa Allgood
(74) *Attorney, Agent, or Firm* — Finnegan, Henderson, Farabow, Garrett & Dunner, LLP

(57) ABSTRACT

According to one embodiment, a sensor includes a first magnetic member, a first counter magnetic member, a first magnetic element, and a first magnetic interconnect. A direction from the first magnetic member to the first counter magnetic member is along a first direction. A first gap is provided between the first magnetic member and the first counter magnetic member. The first magnetic element includes a first magnetic region. A second direction from the first magnetic region to the first gap crosses the first direction. A direction from the first magnetic interconnect to the first magnetic region is along the second direction.

20 Claims, 15 Drawing Sheets

(56) References Cited

U.S. PATENT DOCUMENTS

2021/0123992 A1   4/2021   Harada et al.
2021/0286023 A1   9/2021   Okatake et al.

FOREIGN PATENT DOCUMENTS

| JP | 2019-207167 A | 12/2019 |
| JP | 2021-67568 A | 4/2021 |
| WO | WO 2019/239933 | 12/2019 |
| WO | WO 2020/138170 A1 | 7/2020 |

OTHER PUBLICATIONS

L. Pan et al., "Novel Magnetic Field Modulation Concept Using Multiferroic Heterostructure for Magnetoresistive Sensors," Sensors 20, No. 1440, 13 pages (2020).

\* cited by examiner

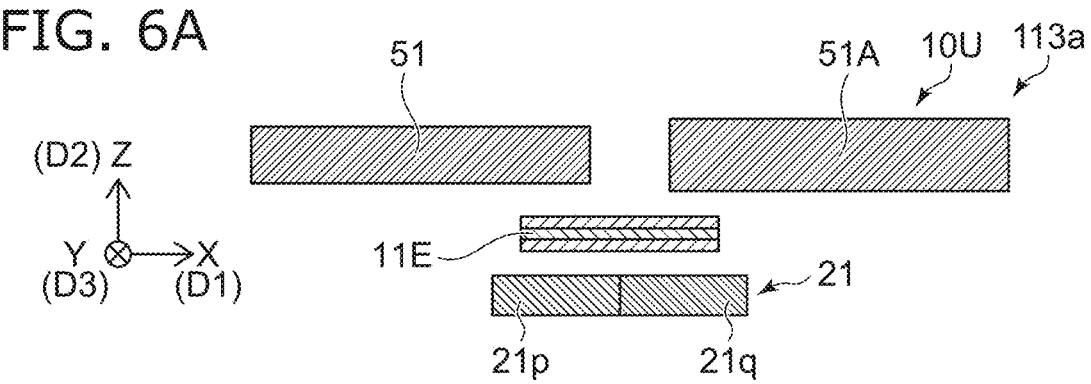
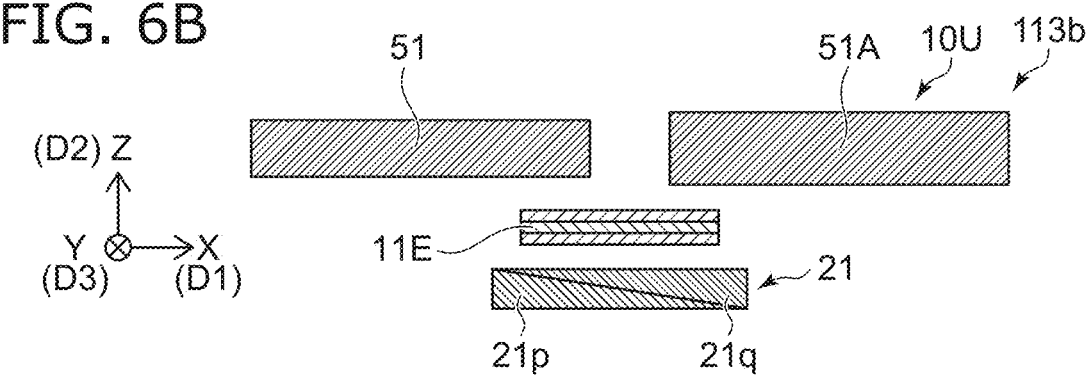

Hsig=0

+Hsig

-Hsig

SENSOR AND INSPECTION DEVICE

CROSS-REFERENCE TO RELATED APPLICATIONS

This application is based upon and claims the benefit of priority from Japanese Patent Application No. 2021-145587, filed on Sep. 7, 2021; the entire contents of which are incorporated herein by reference.

FIELD

Embodiments described herein relate generally to a sensor and an inspection device.

BACKGROUND

There is a sensor that uses a magnetic layer. There is an inspection device that uses a sensor. It is desired to improve the characteristics of the sensor.

BRIEF DESCRIPTION OF THE DRAWINGS

FIGS. 6A and 6B are schematic cross-sectional views illustrating sensors according to the first embodiment;

DETAILED DESCRIPTION

Figure 1A:
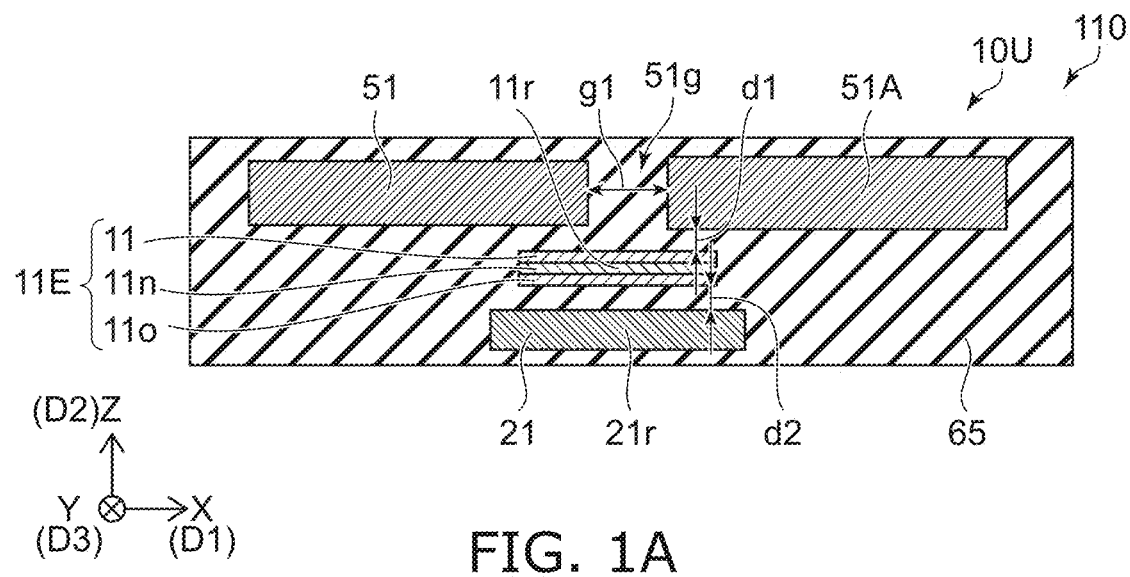
FIGS. 1A and 1B are schematic views illustrating a sensor according to a first embodiment.

According to one embodiment, a sensor includes a first magnetic member, a first counter magnetic member, a first magnetic element, and a first magnetic interconnect. A direction from the first magnetic member to the first counter magnetic member is along a first direction. A first gap is provided between the first magnetic member and the first counter magnetic member. The first magnetic element includes a first magnetic region. A second direction from the first magnetic region to the first gap crosses the first direction. A direction from the first magnetic interconnect to the first magnetic region is along the second direction.

According to one embodiment, an inspection device includes the sensor described above, and a processor configured to process a signal output from the sensor.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1B:
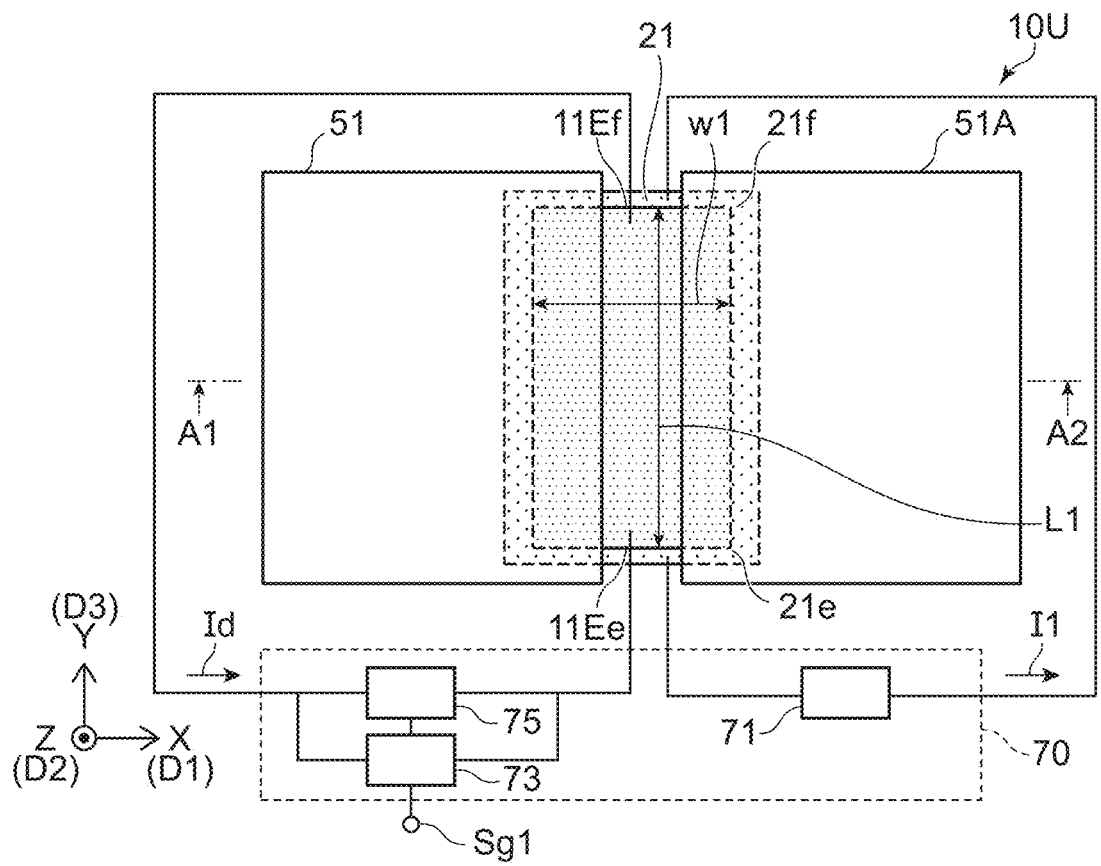

FIGS. 1A and 1B are schematic views illustrating a sensor according to a first embodiment.

FIG. 1A is a cross-sectional view taken along the line A1-A2 of FIG. 1B. FIG. 1B is a plan view.

As shown in FIGS. 1A and 1B, a sensor 110 according to the embodiment includes an element part 10U. The element part 10U includes a first magnetic member 51, a first counter magnetic member 51A, a first magnetic element 11E, and a first magnetic interconnect 21.

A direction from the first magnetic member 51 to the first counter magnetic member 51A is along a first direction D1. The first direction is defines as an X-axis direction. One direction perpendicular to the X-axis direction is defined as a Z-axis direction. A direction perpendicular to the X-axis direction and the Z-axis direction is defined as a Y-axis direction.

As shown in FIG. 1A, a first gap 51g is provided between the first magnetic member 51 and the first counter magnetic member 51A.

As shown in FIG. 1A, the element part 10U may include an insulating member 65. At least a part of the insulating member 65 may be provided in the first gap 51g. In FIG. 1B, the insulating member 65 is omitted.

The first magnetic element 11E includes a first magnetic region 11r. A second direction D2 from the first magnetic region 11r to the first gap 51g crosses the first direction D1. The second direction D2 is, for example, the Z-axis direction. A direction from the first magnetic interconnect 21 to the first magnetic region 11r is along the second direction D2.

The magnetic field to be detected is concentrated by the first magnetic member 51 and the first counter magnetic member 51A and applied to the first magnetic element 11E. For example, the magnetic field that has passed through the first magnetic member 51 passes through the first magnetic element 11E and heads toward the first counter magnetic member 51A. The first magnetic member 51 and the first counter magnetic member 51A function as, for example, an MFC (Magnetic Flux Concentrator). High sensitivity can be obtained by providing the first magnetic member 51 and the first counter magnetic member 51A.

The first magnetic interconnect 21 includes, for example, at least one selected from the group consisting of Fe, Co and Ni.

As shown in FIG. 1B, the sensor 110 may include a control circuit part 70. The control circuit part 70 may include a first current circuit 71. The first current circuit 71 may be provided separately from the sensor 110. The first current circuit 71 is possible to supply the first current I1 to the first magnetic interconnect 21. The first current I1 includes an AC component. The first current I1 is, for example, an alternating current.

For example, the first magnetic interconnect 21 includes a first magnetic interconnect one part 21e and a first magnetic interconnect other part 21f. A third direction D3 from the first magnetic interconnect one part 21e to the first magnetic interconnect other part 21f crosses the plane including the first direction D1 and the second direction D2. The third direction D3 is, for example, the Y-axis direction.

The first current I1 flows in the direction from the first magnetic interconnect one part 21e to the first magnetic interconnect other part 21f, or from the first magnetic interconnect other part 21f to the first magnetic interconnect one part 21e. A magnetic field based on the first current I1 is applied to the first magnetic element 11E. The magnetic field includes a component in the first direction D1.

As the first current I1 including the AC component flows through the first magnetic interconnect 21, the characteristics of the first magnetic interconnect 21 change according to the first current I1. For example, the effective magnetic permeability of the first magnetic interconnect 21 changes according to the first current I1. For example, the current magnetic field generated by the first current I1 includes a component that crosses the direction of high magnetic permeability in the first magnetic interconnect 21. When the first current I1 flows through the first magnetic interconnect 21, the magnetic permeability of the first magnetic interconnect 21 changes. The direction in which the magnetic permeability of the first magnetic interconnect 21 is high corresponds to the third direction D3. For example, the magnetic field to be detected is modulated by the magnetic field generated by the first current I1 and applied to the first magnetic element 11E. As a result, the magnetic field to be detected can be detected with higher sensitivity by suppressing noise.

Figure 2A:
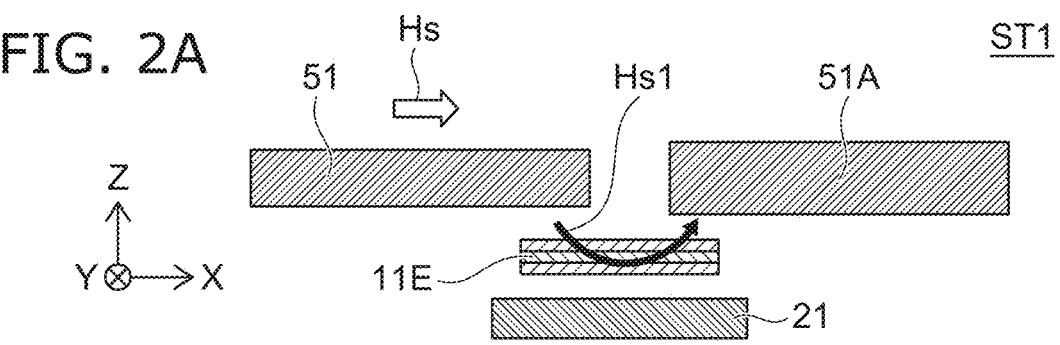
FIGS. 2A and 2B are schematic cross-sectional views illustrating operations of the sensor according to the first embodiment.
Figure 2B:
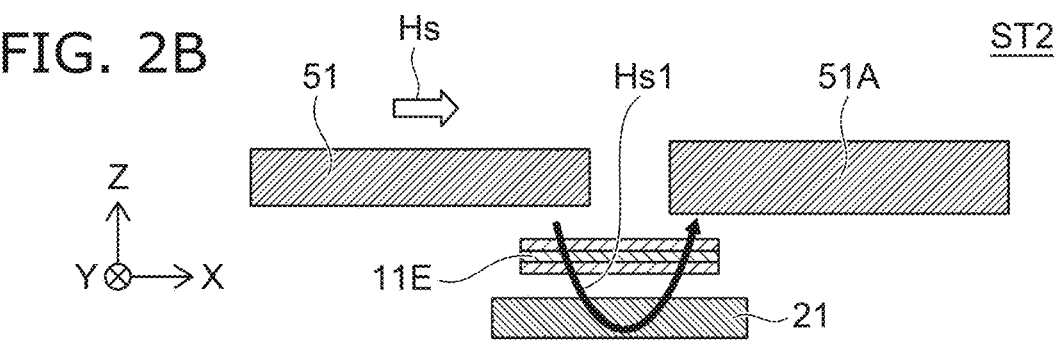

FIGS. 2A and 2B are schematic cross-sectional views illustrating operations of the sensor according to the first embodiment.

As shown in FIGS. 2A and 2B, the first state ST1 and the second state ST2 can be formed in the sensor 110. For example, the first state ST1 corresponds to when the first current I1 is either positive or negative, and the second state ST2 corresponds to when the first current I1 is positive or negative. Alternatively, for example, the absolute value of the first current I1 in the first state ST1 is different from the absolute value of the first current I1 in the second state ST2.

In these two states, the magnetic field Hs to be detected passes through the first magnetic member 51 and the first counter magnetic member 51A. For example, in the first state ST1, the magnetic field Hs1 between the first magnetic member 51 and the first counter magnetic member 51A is unlikely to pass through the first magnetic element 11E. For example, in the second state ST2, the magnetic field Hs1 easily passes through the first magnetic element 11E. The strength of the magnetic field Hs1 passing through the first magnetic element 11E differs between the first state ST1 and the second state ST2. In this way, the magnetic field Hs1 modulated by the first current I1 is applied to the first magnetic element 11E.

For example, the frequency of the AC component of the first current I1 is set higher than the frequency of the magnetic field Hs to be detected (in the case of direct current, the frequency is set to 0). The magnetic field Hs1 in which the magnetic field Hs is modulated into harmonics is applied to the first magnetic element 11E. The electrical resistance of the first magnetic element 11E changes according to the magnetic field Hs1 applied to the first magnetic element 11E. In the embodiment, the electrical resistance of the first magnetic element 11E changes according to the magnetic field Hs1 modulated by the harmonics. For example, a change in the electrical resistance of the first magnetic element 11E is detected, and the detected signal is demodulated (for example, detected) based on the frequency of the AC component. During demodulation, at least some of the noise is removed. As a result, the magnetic field Hs to be detected can be detected while suppressing noise.

As described above, in the embodiment, the magnetic field Hs to be detected is modulated by the first magnetic interconnect 21 and applied to the first magnetic element 11E. Noise can be suppressed by modulation and demodulation. According to the embodiment, it is possible to provide a sensor whose characteristics can be improved.

As shown in FIG. 1 (b), in this example, the control circuit part 70 further includes an element circuit 75. The element circuit 75 may be provided separately from the sensor 110. The element circuit 75 is configured to supply the element current Id to the first magnetic element 11E.

The first magnetic element 11E includes a first magnetic element one end part 11Ee and a first magnetic element other end part 11Ef. The first magnetic interconnect one part 21e corresponds to, for example, the first magnetic element one end part 11Ee. The first magnetic interconnect other part 21f corresponds to the first magnetic element other end part 11Ef. For example, in the second direction D2, the first magnetic interconnect one part 21e may overlap the first magnetic element one end part 11Ee. In the second direction D2, the first magnetic interconnect other part 21f may overlap the first magnetic element other end part 11Ef.

The element current Id flows from, for example, the first magnetic element one end part 11Ee to the first magnetic element other end part 11Ef. The electrical resistance of the first magnetic element 11E and the change in the electrical resistance can be detected by the element current Id. In the embodiment, electrical resistance may be detected by constant current or constant voltage operation.

As shown in FIG. 1B, the control circuit part 70 may include a detection circuit 73. The detection circuit 73 may be provided separately from the sensor 110. The detection circuit 73 is electrically connected to, for example, the first magnetic element one end part 11Ee and the first magnetic element other end part 11Ef. The detection circuit 73 can detect a change in potential between the first magnetic element one end part 11Ee and the first magnetic element other end part 11Ef. The change in potential depends on the magnetic field Hs1 modulated according to the first current I1 flowing through the first magnetic interconnect 21. The detection circuit 73 can, for example, demodulate the change in potential and output the signal Sg1 according to the magnetic field Hs to be detected. Demodulation is performed based on the frequency of the AC component of the first current I1.

As shown in FIG. 1A, the first magnetic element 11E includes a first magnetic layer 11, a first counter magnetic layer 110, and a first non-magnetic layer 11n. The first non-magnetic layer 11n is provided between the first magnetic layer 11 and the first counter magnetic layer 110. For example, a direction from the first opposed magnetic layer 110 to the first magnetic layer 11 is along the second direction D2. The first non-magnetic layer 11n includes, for example, at least one selected from the group consisting of Cu, Au and Ag. The first magnetic element 11E is, for example, a GMR (Giant Magneto Resistive effect) element. In the embodiment, the first non-magnetic layer 11n may be insulating. For example, the first non-magnetic layer 11n may include MgO. The first magnetic element 11E may be a TMR (Tunnel Magneto Resistive) element.

For example, a position of the first magnetic element 11E in the second direction D2 is between a position of the first magnetic interconnect 21 in the second direction D2 and a position of the first magnetic member 51 in the second direction D2. The position of the first magnetic element 11E in the second direction D2 is between the position of the first magnetic interconnect 21 in the second direction D2 and a position of the first counter magnetic member 51A in the second direction D2.

The position of the first magnetic interconnect 21 in the second direction D2 may be between the position of the first magnetic element 11E in the second direction D2 and the position of the first magnetic member 51 in the second direction D2. The position of the first magnetic interconnect 21 in the second direction D2 may be between the position of the first magnetic element 11E in the second direction D2 and the position of the first counter magnetic member 51A in the second direction D2.

As shown in FIG. 1A, for example, a part of the first magnetic element 11E may overlap the first magnetic member 51 in the second direction D2. Another part of the first magnetic element 11E may overlap the first counter magnetic member 51A in the second direction D2. For example, a part of the first magnetic element 11E is between a part of the first magnetic interconnect 21 and the first magnetic member 51 in the second direction D2. Another part of the first magnetic element 11E is between another part of the first magnetic interconnect 21 and the first counter magnetic member 51A in the second direction D2.

As shown in FIG. 1A, a distance between the first magnetic member 51 and the first counter magnetic member 51A along the first direction D1 is defined as a distance g1. The distance g1 may be, for example, not less than 1 μm and not more than 30 μm. A distance between the first magnetic element 11E and the first counter magnetic member 51A (or first magnetic member 51) is defined as a distance d1. The distance d1 may be, for example, not less than 1 μm and not more than 30 μm. The distance d1 may be, for example, not less than 0.3 μm and not more than 30 μm. A distance between the first magnetic interconnect 21 and the first magnetic element 11E is defined as a distance d2. The distance d2 may be, for example, not less than 1 μm and not more than 3 μm. The distance d2 may be, for example, not less than 0.3 μm and not more than 3 μm.

As shown in FIG. 1B, a length L1 of the first magnetic element 11E along the third direction D3 is longer than a length w1 (for example, width) of the first magnetic element 11E along the first direction D1. For example, stable magnetization can be easily obtained.

Figure 3:
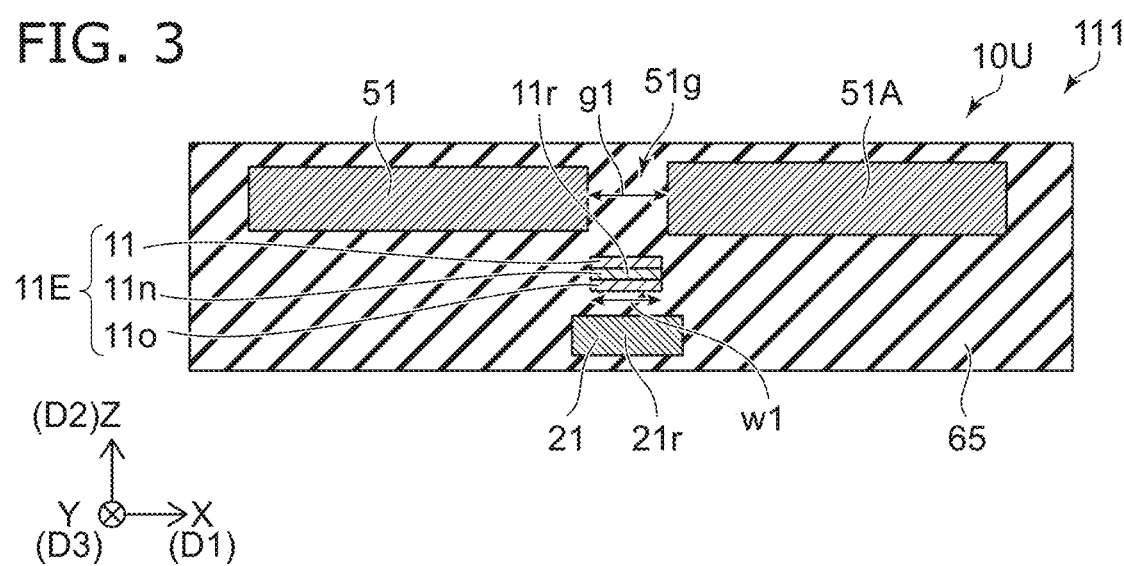
FIG. 3 is a schematic cross-sectional view illustrating a sensor according to the first embodiment.
Figure 4A:
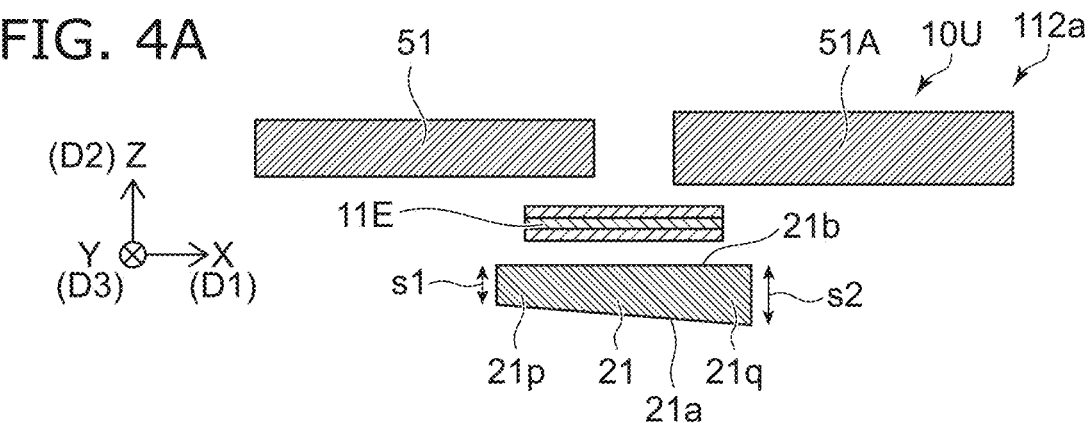
FIGS. 4A to 4D are schematic cross-sectional views illustrating sensors according to the first embodiment.
Figure 4B:
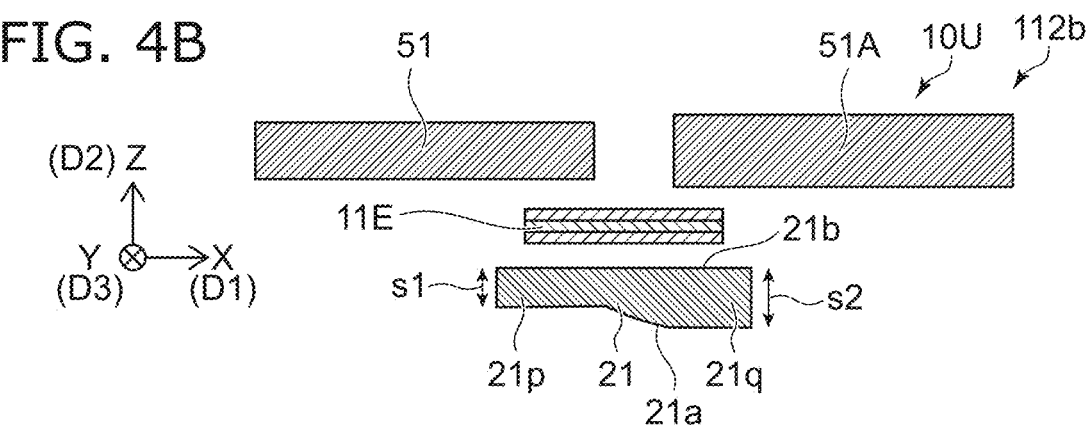
Figure 4C:
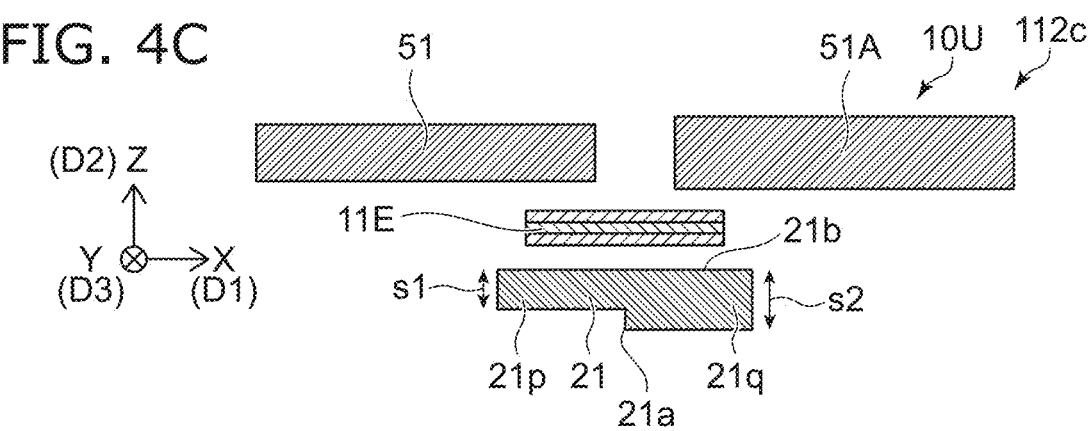
Figure 4D:
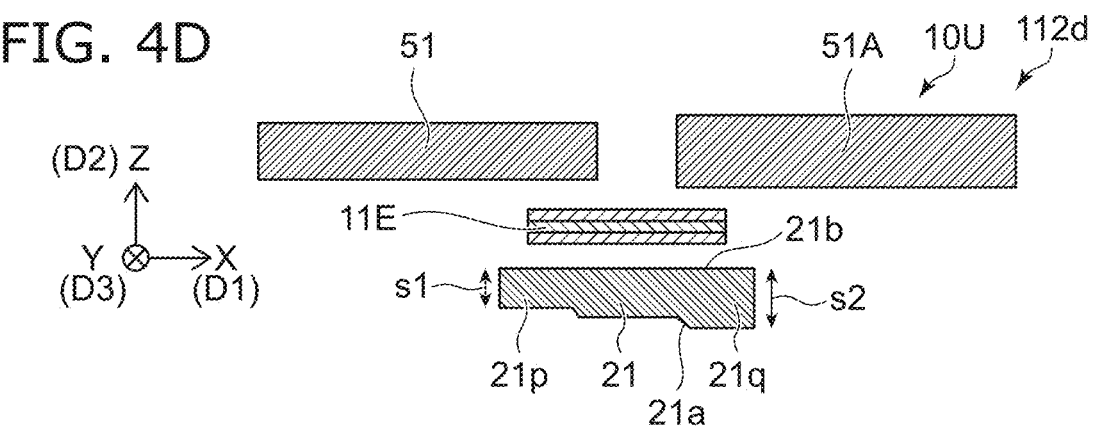
Figure 5A:
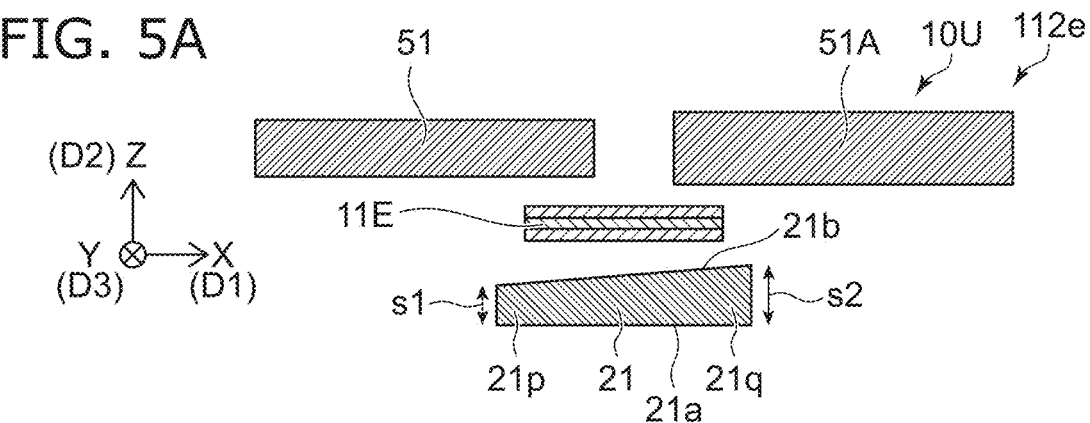
FIGS. 5A to 5D are schematic cross-sectional views illustrating sensors according to the first embodiment.
Figure 5B:
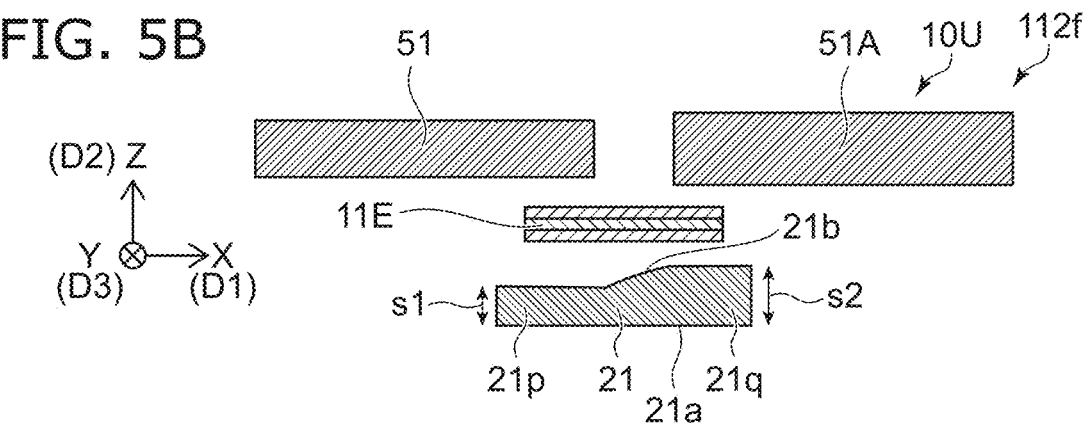
Figure 5C:
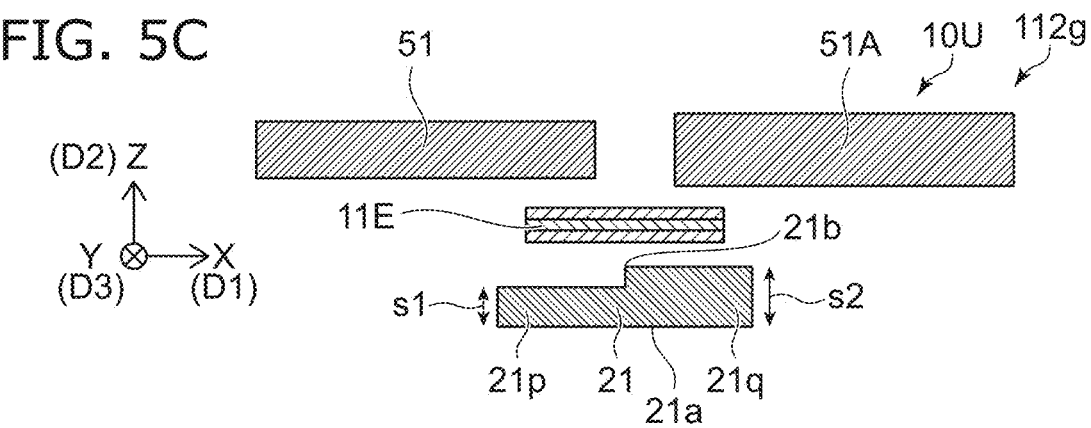
Figure 5D:
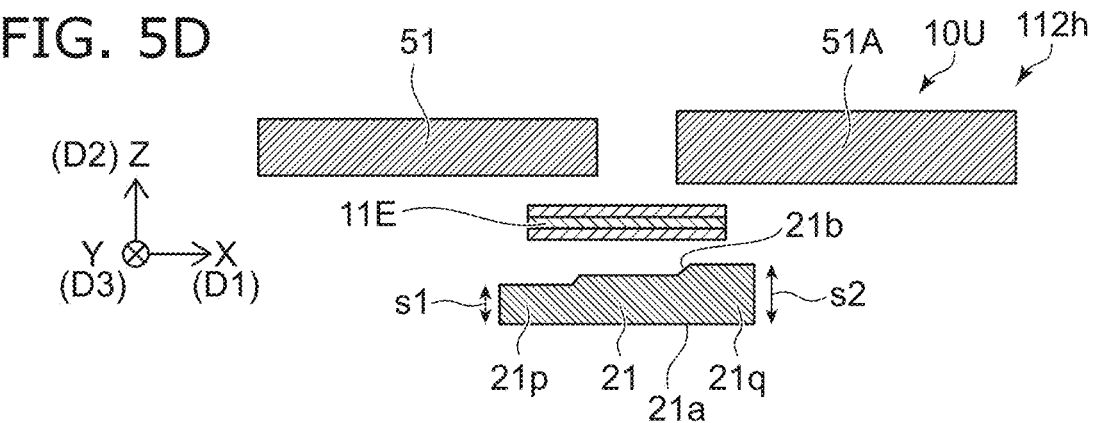

FIG. 3 is a schematic cross-sectional view illustrating a sensor according to the first embodiment.

As shown in FIG. 3, in a sensor 111 according to the embodiment, the configuration of the first magnetic element 11E is different from the configuration of the sensor 110. The configuration of the sensor 111 other than this may be the same as the configuration of the sensor 110.

In the sensor 111, the first magnetic element 11E does not overlap the first magnetic member 51 and does not overlap the first counter magnetic member 51A in the second direction D2. Also in this case, the modulated magnetic field Hs1 (see FIG. 2A and the like) is applied to the first magnetic element 11E.

For example, the distance g1 between the first magnetic member 51 and the first counter magnetic member 51A along the first direction D1 may be the same as the length w1 (for example, width) along the first direction D1 of the first magnetic element 11E. The distance g1 may be larger than the length w1.

FIGS. 4A to 4D are schematic cross-sectional views illustrating sensors according to the first embodiment.

As shown in FIGS. 4A to 4D, in sensors 112a to 112d according to the embodiment, the first magnetic interconnect 21 includes a first surface 21a and a second surface 21b. A position of the second surface 21b in the second direction D2 is between a position of the first surface 21a in the second direction D2 and the position of the first magnetic member 51 in the second direction D2. At least a part of the first surface 21a is non-parallel to at least a part of the second surface 21b. At least a part of the first surface 21a may be inclined with respect to the X-Y plane.

In the sensors 112a to 112d, at least a part of the first surface 21a crosses the X-Y plane. On the other hand, the second surface 21b is substantially parallel to the X-Y plane.

For example, the first magnetic interconnect 21 includes a first partial region 21p and a second partial region 21q. A direction from the first partial region 21p to the second partial region 21q is along the first direction D1. A first thickness s1 along the second direction D1 of the first partial region 21p is different from a second thickness s2 along the second direction D2 of the second partial region 21q.

In the sensors 112a to 112d, the first thickness s1 is thinner than the second thickness s2. In the sensor 112a, the thickness changes continuously. In the sensor 112b, the thickness changes in one step. The change is gradual. In the sensor 112c, the thickness changes discontinuously in one step. In the sensor 112d, the thickness changes in two steps.

FIGS. 5A to 5D are schematic cross-sectional views illustrating sensors according to the first embodiment.

As shown in FIGS. 5A to 5D, in sensors 112e to 112h according to the embodiment, the first magnetic interconnect 21 includes the first surface 21a and the second surface 21b. At least a part of the first surface 21a is non-parallel to at least a part of the second surface 21b.

In the sensors 112e to 112h, at least a part of the second surface 21b crosses the X-Y plane. On the other hand, the first surface 21a is substantially parallel to the X-Y plane.

For example, the first magnetic interconnect 21 includes the first partial region 21p and the second partial region 21q. The first thickness s1 along the second direction D1 of the first partial region 21p is different from the second thickness s2 along the second direction D2 of the second partial region 21q.

In the sensors 112e to 112h, the first thickness s1 is thinner than the second thickness s2. In the sensor 112e, the thickness changes continuously. In the sensor 112f, the thickness changes in one step. The change is gradual. In the sensor 112g, the thickness changes discontinuously in one step. In the sensor 112h, the thickness changes in two steps.

In the sensors 112a to 112h, the thickness of the first magnetic interconnect 21 (the length along the second direction D2) changes along the first direction D1. By supplying the first current I1 including an AC component to the first magnetic interconnect 21, the effective magnetic permeability of the first magnetic interconnect 21 is likely to change effectively and stably. For example, formation of multiple magnetic domains is more effectively suppressed. Stable modulation is easy to be performed.

FIGS. 6A and 6B are schematic cross-sectional views illustrating sensors according to the first embodiment.

As shown in FIGS. 6A and 6B, in sensors 113a and 113b according to the embodiment, the first magnetic interconnect 21 includes the first partial region 21p and the second partial region 21q. The direction from the first partial region 21p to the second partial region 21q is along the first direction D1. A material of at least a part of the first partial region 21p is different from a material of at least a part of the second partial region 21q.

In the sensors 113a and 113b, the material of the first magnetic interconnect 21 changes in the first direction D1. By supplying the first current I1 including an AC component to the first magnetic interconnect 21, the effective magnetic permeability of the first magnetic interconnect 21 is likely to change effectively and stably. For example, formation of multiple magnetic domains is more effectively suppressed. Stable modulation is easy to be performed.

Boundaries of multiple regions of different materials, such as the sensor 113b, may cross (eg, tilt) the X-Y plane.

In the sensors 112a to 112h, 113a and 113b, the first partial region 21p may overlap the first magnetic member 51 in the second direction D2. The second partial region 21q may overlap the first counter magnetic member 51A in the second direction D2.

The configurations of the sensors 112a to 112h, 113a and 113b other than the above may be the same as the configurations of the sensors 110 and 111.

Hereinafter, an example of the characteristics of the first magnetic element 11E in the above sensor will be described.

Figure 7A:
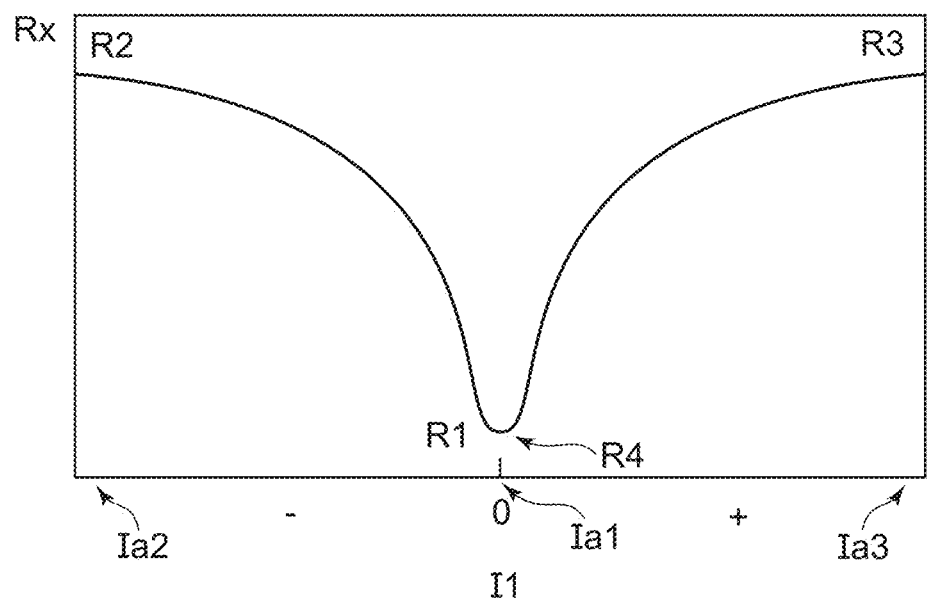
FIGS. 7A and 7B are schematic views illustrating characteristics of the sensor according to the first embodiment.
Figure 7B:
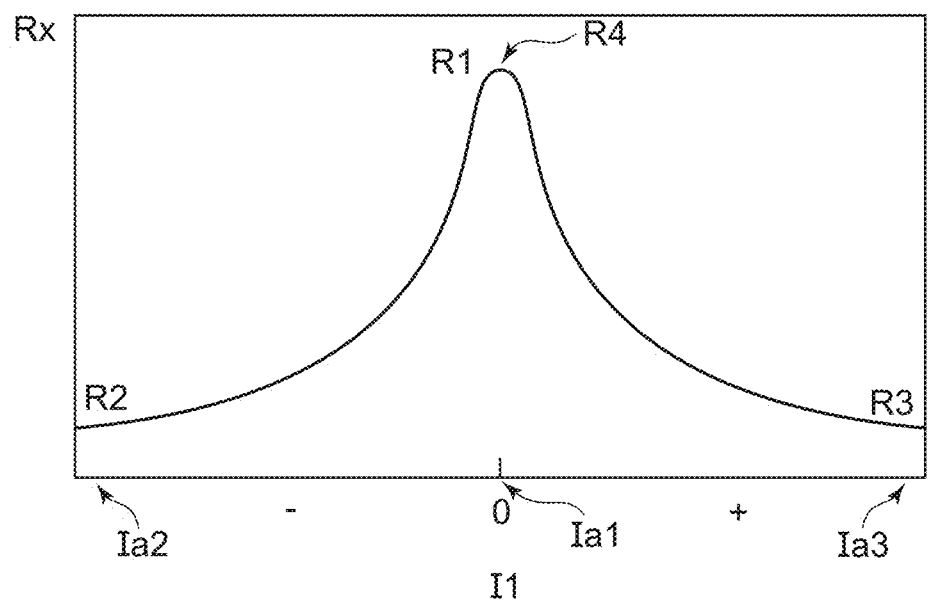

FIGS. 7A and 7B are schematic views illustrating characteristics of the sensor according to the first embodiment;

The horizontal axis of these figures corresponds to the value of the first current I1 flowing through the first magnetic interconnect 21. The vertical axis is the electrical resistance Rx of the first magnetic element 11E. As shown in FIGS. 7A and 7B, in the embodiment, the electrical resistance Rx shows the characteristic of an even function with respect to the change of the first current I1.

For example, the electrical resistance Rx of the first magnetic element 11E is a first resistance value R1 when the first current I1 is a first value current Ia1. The electrical resistance Rx is a second resistance value R2 when the first current I1 is a second value current Ia2. The electrical resistance Rx is a third resistance value R3 when the first current I1 is a third value current Ia3. The orientation of the second value current Ia2 is opposite to the orientation of the third value current Ia3. The absolute value of the first value current Ia1 is smaller than the absolute value of the second value current Ia2 and smaller than the absolute value of the third value current Ia3. The first value current Ia1 may be, for example, substantially 0.

In the example of FIG. 7A, the first resistance value R1 is lower than the second resistance value R2 and lower than the third resistance value R3. The first resistance value R1 is, for example, the minimum value of electrical resistance. In the example of FIG. 7B, the first resistance value R1 is higher than the second resistance value R2 and higher than the third resistance value R3. The first resistance value R1 is, for example, the maximum value of electrical resistance.

For example, the electrical resistance Rx is a fourth resistance value R4 when a current does not substantially flow through the first magnetic interconnect 21. For example, the first resistance value R1 may be substantially the same as the fourth resistance value R4 when no current flows substantially. For example, a ratio of the absolute value of the difference between the first resistance value R1 and the fourth resistance value R4 to the fourth resistance value R4 is 0.01 or less. The ratio may be not more than 0.001. For positive and negative currents, the characteristics of an even function can be obtained.

Such a relationship between the first current I1 and the electric resistance Rx is based on that the magnetic field due to the first current I1 is applied to the first magnetic element 11E, and the electrical resistance Rx of the first magnetic element 11E changes depending on the strength of the magnetic field.

The electrical resistance Rx when an external magnetic field is applied to the first magnetic element 11E also shows the characteristics of an even function as in the example shown in FIG. 7A or FIG. 7B.

Figure 8A:
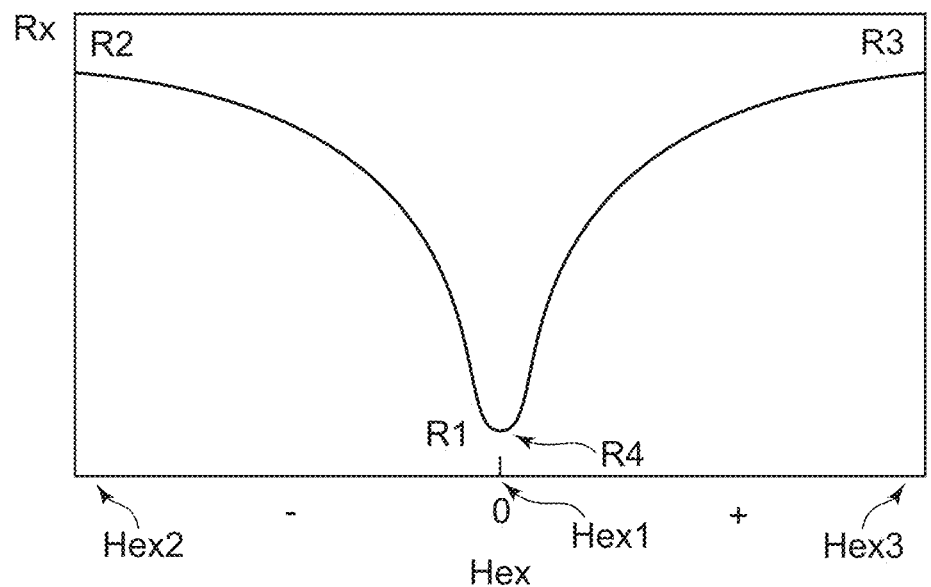
FIGS. 8A and 8B are schematic views illustrating characteristics of the sensor according to the first embodiment.
Figure 8B:
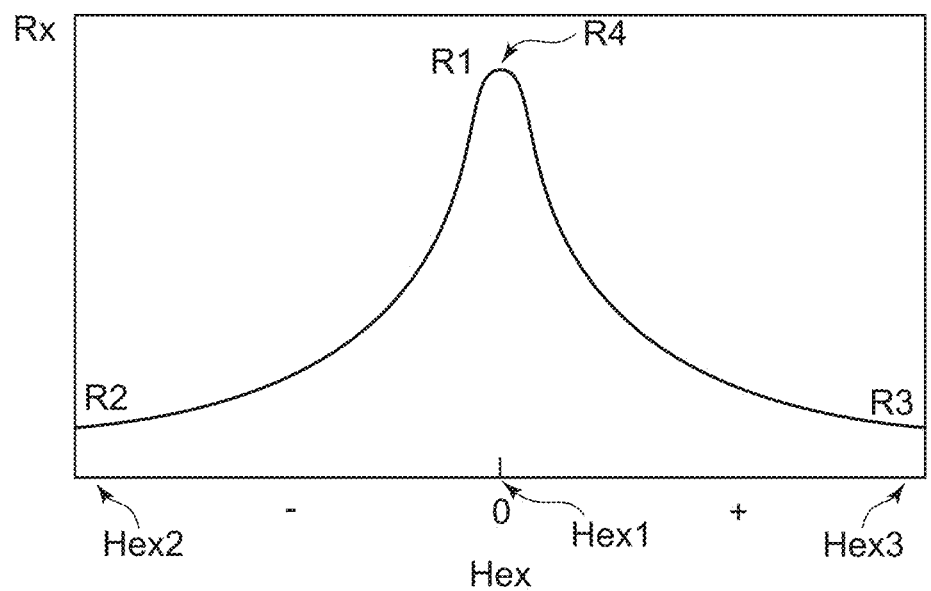

FIGS. 8A and 8B are schematic views illustrating characteristics of the sensor according to the first embodiment.

The horizontal axis of these figures is the strength of the external magnetic field Hex applied to the first magnetic element 11E. The vertical axis is the electrical resistance Rx of the first magnetic element 11E. These figures correspond to the RH characteristics. As shown in FIGS. 8A and 8B, the electric resistance Rx has the property of even function with respect to a magnetic field applied to the first magnetic element 11E (external magnetic field Hex, for example, a magnetic field including a component in the X-axis direction).

As shown in FIGS. 8A and 8B, the electrical resistance Rx of the first magnetic element 11E is the first resistance value R1 when the first magnetic field Hex1 is applied to the first magnetic element 11E. The electrical resistance Rx is the second resistance value R2 when the second magnetic field Hex2 is applied to the first magnetic element 11E. The electric resistance Rx is the third resistance value R3 when the third magnetic field Hex3 is applied to the first magnetic element 11E. The orientation of the second magnetic field Hex2 is opposite to the orientation of the third magnetic field Hex3. The absolute value of the first magnetic field Hex1 is smaller than the absolute value of the second magnetic field Hex2 and smaller than the absolute value of the third magnetic field Hex3.

In the example of FIG. 8A, the first resistance value R1 is lower than the second resistance value R2 and lower than the third resistance value R3. In the example of FIG. 8B, the first resistance value R1 is higher than the second resistance value R2 and higher than the third resistance value R3. For example, when the external magnetic field Hex is not applied to the first magnetic element 11E, the electrical resistance Rx is the fourth resistance value R4. The first resistance value R1 is substantially the same as the fourth resistance value R4 when the external magnetic field Hex is not applied. For example, a ratio of the absolute value of the difference between the first resistance value R1 and the fourth resistance value R4 to the fourth resistance value R4 is not more than 0.01. The ratio may be not more than 0.001. Substantially even function characteristics are obtained for positive and negative external magnetic fields.

Utilizing such characteristics of even functions, high-sensitivity detection is possible as follows.

In the following, an example will be described in which the first current I1 is an alternating current and does not substantially include a DC component. A first current I1 (alternating current) is supplied to the first magnetic interconnect 21, and an alternating magnetic field generated by the alternating current is applied to the first magnetic element 11E. An example of the change in the electrical resistance Rx at this time will be described.

Figure 9A:
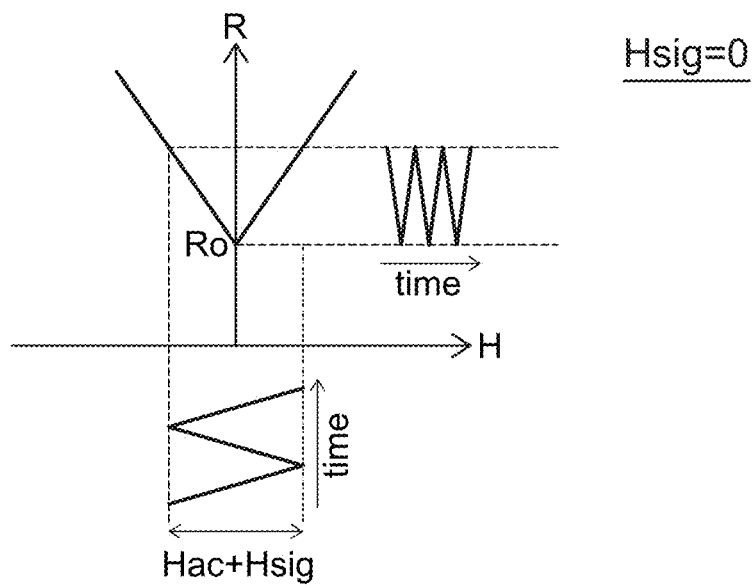
FIGS. 9A to 9C are graphs illustrating characteristics of the sensor according to the first embodiment.
Figure 9B:
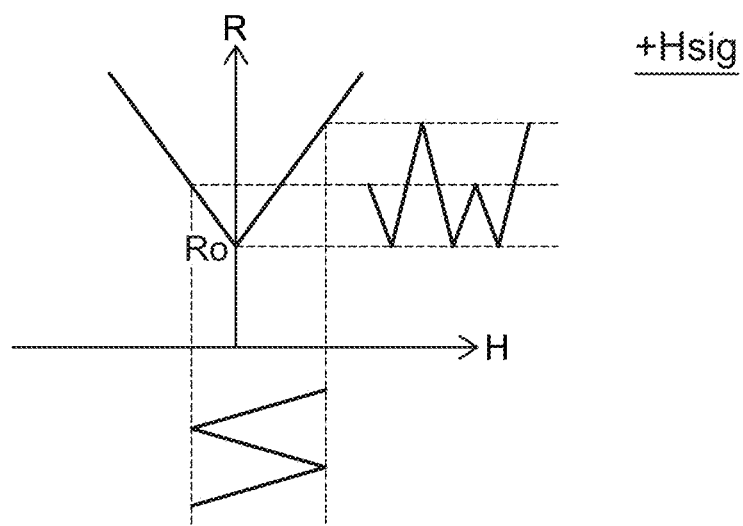

FIGS. 9A and 9B are graphs illustrating characteristics of the sensor according to the first embodiment.

Figure 9C:
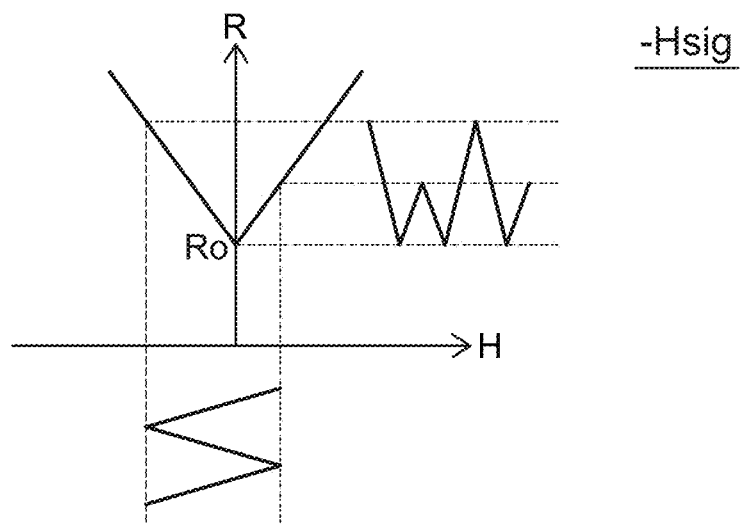

FIG. 9A shows the characteristics when the signal magnetic field Hsig (external magnetic field) applied to the first magnetic element 11E is 0. FIG. 9B shows the characteristics when the signal magnetic field Hsig is positive. FIG. 9C shows the characteristics when the signal magnetic field Hsig is negative. These figures show the relationship between the magnetic field H and the resistance R (corresponding to electrical resistance Rx).

As shown in FIG. 9A, when the signal magnetic field Hsig is 0, the resistance R exhibits a characteristic symmetric with respect to the positive and negative magnetic fields H. When the alternating magnetic field Hac is zero, the resistance R is a low resistance Ro. For example, the magnetization of the magnetic layer included in the first magnetic element 11E rotates in substantially the same manner with respect to the positive and negative magnetic fields H. Therefore, a symmetrical change in resistance can be obtained. The fluctuation of the resistance R with respect to the alternating magnetic field Hac has the same value for positive and negative polarities. The period of change of the resistance R is ½ times the period of the alternating magnetic field Hac. The frequency of change of the resistance R is twice the frequency of the alternating magnetic field Hac. The change of the resistance R has substantially no frequency component of the alternating magnetic field Hac.

As shown in FIG. 9B, when a positive signal magnetic field Hsig is applied, the characteristic of the resistance R shifts to a side of the positive magnetic field H. In the alternating magnetic field Hac on the positive side, for example, the resistance R becomes high. In the alternating magnetic field Hac on the negative side, the resistance R becomes low.

As shown in FIG. 9C, when a negative signal magnetic field Hsig is applied, the characteristic of the resistance R shifts to a side of the negative magnetic field H. In the alternating magnetic field Hac on the positive side, for example, the resistance R becomes low. In the alternating magnetic field Hac on the negative side, the resistance R becomes high.

When a signal magnetic field Hsig of a predetermined magnitude is applied, the resistance R fluctuates differently with respect to the positive and negative of the alternating magnetic field Hac. The period of fluctuation of the resistance R with respect to the alternating magnetic field Hac or negative is the same as the period of the alternating magnetic field Hac. The component of the alternating magnetic field Hac in the obtained output voltage becomes a voltage corresponding to the signal magnetic field Hsig.

The above characteristics are obtained when the signal magnetic field Hsig does not change with time. When the signal magnetic field Hsig changes with time at a frequency lower than that of the AC magnetic field Hac, it becomes as follows. The frequency of the signal magnetic field Hsig is defined as a signal frequency fsig. The frequency of the alternating magnetic field Hac is defined as an alternating frequency fac. At this time, an output corresponding to the signal magnetic field Hsig is generated at a frequency of fac±fsig.

When the signal magnetic field Hsig changes with time, the signal frequency fsig is, for example, not more than 1 kHz. On the other hand, the alternating frequency fac is sufficiently higher than the signal frequency fsig. For example, the alternating frequency fac is not less than 10 times the signal frequency fsig.

For example, the signal magnetic field Hsig can be detected with high accuracy by extracting the output voltage of a component (AC frequency component) having the same frequency as the frequency of the alternating magnetic field Hac. In the sensor 110 according to the embodiment, it is possible to detect the external magnetic field Hex (signal magnetic field Hsig) generated from the detection target with high sensitivity by utilizing such characteristics.

In the embodiment, as described with respect to FIGS. 2A and 2B, the magnetic field Hs to be detected is modulated by the first current I1 flowing through the first magnetic interconnect 21 and applied to the first magnetic element 11E. In addition to the modulation of the twice high frequency of the magnetic field Hs to be detected, the modulation of the high frequency of the first magnetic element 11E having the even function characteristic is performed. By demodulating the detection result based on such modulation, noise can be further suppressed. Higher sensitivity detection is possible. A sensor that can improve the characteristics can be provided.

In the embodiment, the element part 10U may include a half bridge or a full bridge.

Figures 10A, 10B:
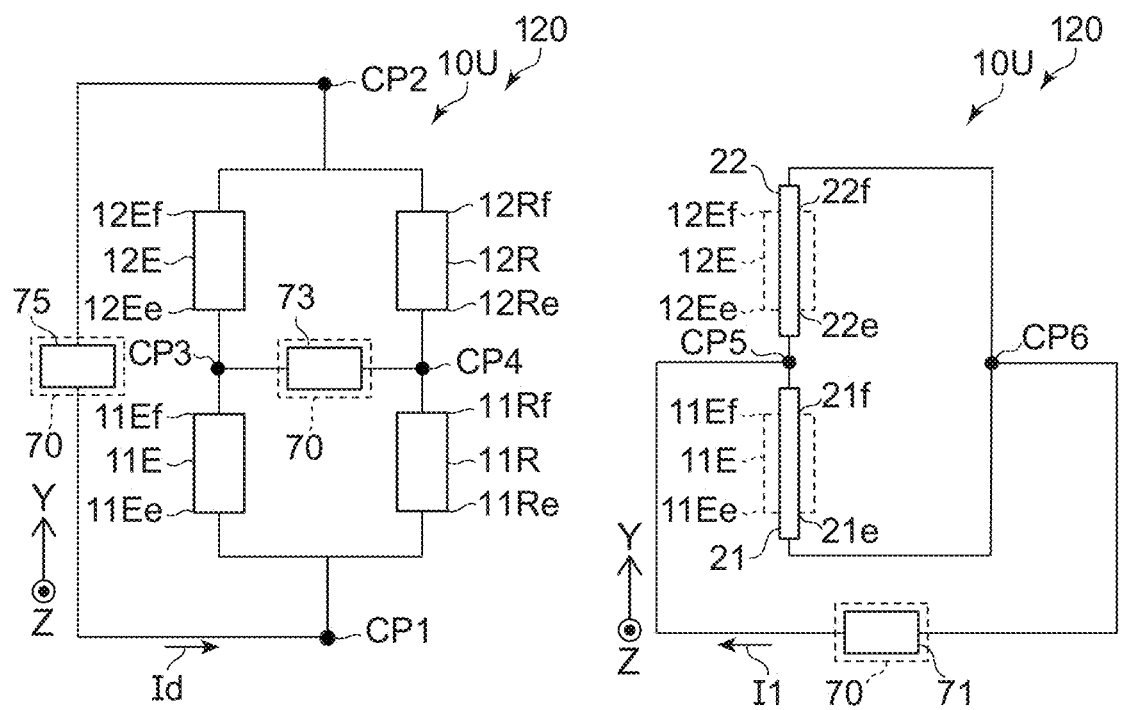
FIGS. 10A and 10B are schematic plan views illustrating a sensor according to the first embodiment.

FIGS. 10A and 10B are schematic plan views illustrating a sensor according to the first embodiment.

As shown in FIG. 10A, in a sensor 120 according to the embodiment, the element part 10U includes the first magnetic element 11E including the first magnetic element one end part 11Ee and the first magnetic element other end part 11Ef, a second magnetic element 12E including a second magnetic element one end part 12Ee and a second magnetic element other end part 12Ef, a first resistance element 11R including a first resistance element one end part 11Re and a first resistance element other end part 11Rf, and a second resistance element 12R including a resistance element one end part 12Re and a second resistance element other end part 12Rf.

The first magnetic element one end part 11Ee is electrically connected to the first resistance element one end part 11Re. The second magnetic element one end part 12Ee is electrically connected to the first magnetic element other end part 11Ef. The second resistance element one end part 12Re is electrically connected to the first resistance element other end part 11Rf. The second magnetic element other end part 12Ef is electrically connected to the second resistance element other end part 12Rf.

As shown in FIG. 10B, the first current circuit 71 is configured to supply the first current I1 to the second magnetic interconnect 21. As shown in FIG. 10A, the control circuit part 70 includes the detection circuit 73. The detection circuit 73 is configured to detect a change in potential between the first magnetic element other end part 11Ef and the first resistance element other end part 11Rf. The detection circuit 73 is configured to detect the change in potential between a connection point CP3 of the first magnetic element other end part 11Ef and the second magnetic element one end part 12Ee, and a connection point CP4 of the first resistance element other end part 11Rf and the second resistance element one end part 12Re.

As shown in FIG. 10A, the control circuit part 70 may include the element circuit 75. The element circuit 75 is configured to supply the element current Id between a connection point CP1 of the first magnetic element one end part 11Ee and the first resistance element one end part 11Re, and a connection point CP2 of the second magnetic element other end part 12Ef and the second resistance element other end part 12Rf. In the embodiment, the electrical resistance may be detected by the constant current or the constant voltage operation.

As shown in FIG. 10B, the element part 10U includes the first magnetic interconnect 21 and a second magnetic interconnect 22. The first magnetic interconnect 21 includes the first magnetic interconnect one part 21e corresponding to the first magnetic element one end part 11Ee and the first magnetic interconnect other part 21f corresponding to the first magnetic element other end part 11Ef. The second magnetic interconnect 22 includes a second magnetic interconnect one part 22e corresponding to the second magnetic element one end part 12Ee and a second magnetic interconnect other part 22f corresponding to the second magnetic element other end part 12Ef.

When the first current I1 is flowing in the orientation from the first magnetic interconnect other part 21f to the first magnetic interconnect one part 21e, the first current I1 flows in the orientation from the second magnetic interconnect one part 22e to the second magnetic interconnect other part 22f.

For example, the first current circuit 71 supplies the first current I1 between a connection point CP5 of the first magnetic interconnect other part 21f and the second magnetic interconnect one part 22e, and a connection point CP6 of the first magnetic interconnect one part 21e and the second magnetic interconnect other part 22f.

FIG. 11, and FIGS. 12A to 12D are schematic plan views illustrating sensors according to the first embodiment.

Figure 11:
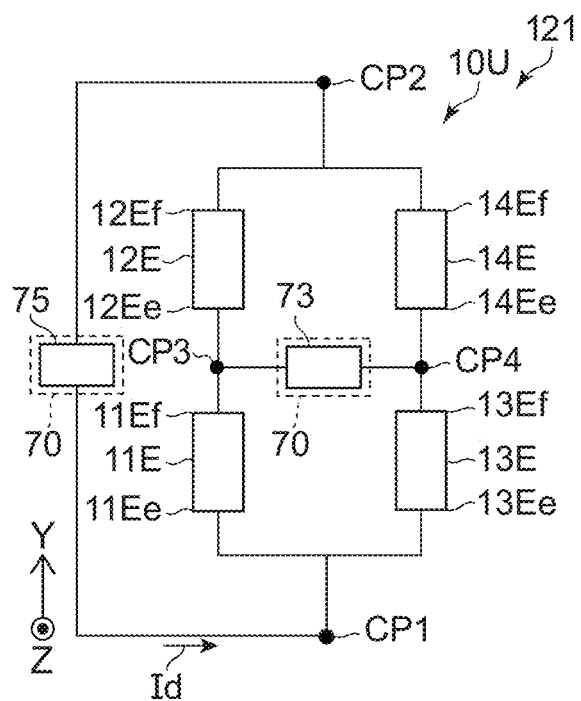
FIG. 11 is a schematic plan view illustrating a sensor according to the first embodiment.

As shown in FIG. 11, in a sensor 121 according to the embodiment, the element part 10U includes a first magnetic element 11E including the first magnetic element one end part 11Ee and the first magnetic element other end part 11Ef, a second magnetic element 12E including the second magnetic element one end part 12Ee and the second magnetic element other end part 12Ef, a third magnetic element 13E including a third magnetic element one end part 13Ee and a third magnetic element other end part 13Ef, and a fourth magnetic element 14E including a fourth magnetic element one end part 14Ee and a fourth magnetic element other end part 14Ef.

The first magnetic element one end part 11Ee is electrically connected to the third magnetic element one end part 13Ee. The second magnetic element one end part 12Ee is electrically connected to the first magnetic element other end part 11Ef. The fourth magnetic element one end part 14Ee is electrically connected to the third magnetic element other end part 13Ef. The second magnetic element other end part 12Ef is electrically connected to the fourth magnetic element other end part 14Ef.

Figure 12A:
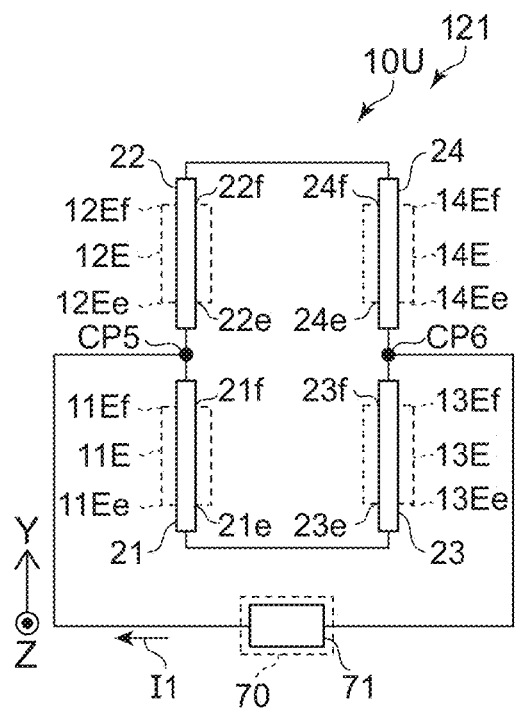
FIGS. 12A to 12D are schematic plan views illustrating sensors according to the first embodiment.

As shown in FIG. 12A, the first current circuit 71 is configured to supply the first current I1 to the first magnetic interconnect 21, the second magnetic interconnect 22, a third magnetic interconnect 23, and a fourth magnetic interconnect 24.

As shown in FIG. 11, the control circuit part 70 includes the detection circuit 73. The detection circuit 73 is configured to detect a change in potential between the first magnetic element other end part 11Ef and the third magnetic element other end part 13Ef. For example, the detection circuit 73 detects a change in potential between the connection point CP3 of the first magnetic element the other end part 11Ef and the second magnetic element one end part 12Ee, and the connection point CP4 of the third magnetic element other end part 13Ef and the fourth magnetic element one end part 14Ee.

As shown in FIG. 11, the control circuit part 70 may include the element circuit 75. The element circuit 75 is configured to supply the element current Id between the connection point CP1 of the first magnetic element one end part 11Ee and the third magnetic element one end part 13Ee, and the connection point CP2 of the second magnetic element other end part 12Ef and the fourth magnetic element other end part 14Ef.

As shown in FIG. 12A, for example, the element part 10U includes the first magnetic interconnect 21, the second magnetic interconnect 22, the third magnetic interconnect 23, and the fourth magnetic interconnect 24. The first magnetic interconnect 21 includes the first magnetic interconnect one part 21e corresponding to the first magnetic element one end part 11Ee and the first magnetic interconnect other part 21f corresponding to the first magnetic element other end part 11Ef. The second magnetic interconnect 22 includes the second magnetic interconnect one part 22e corresponding to the second magnetic element one end part 12Ee and the second magnetic interconnect other part 22f corresponding to the second magnetic element other end part 12Ef. The third magnetic interconnect 23 includes a third magnetic interconnect one part 23e corresponding to the third magnetic element one end part 13Ee and a third magnetic interconnect other part 23f corresponding to the third magnetic element other end part 13Ef. The fourth magnetic interconnect 24 includes a fourth magnetic interconnect one part 24e corresponding to the fourth magnetic element one end part 14Ee and a fourth magnetic interconnect other part 24f corresponding to the fourth magnetic element other end part 14Ef.

When the first current I1 is flowing in the orientation from the first magnetic interconnect other part 21f to the first magnetic interconnect one part 21e, the first current I1 flows in the orientation from the second magnetic interconnect one part 22e to the second magnetic interconnect other part 22f, the first current I1 flows in the orientation from the third magnetic interconnect one part 23e to the third magnetic interconnect other part 23f, and the first current I1 flows in the orientation from the fourth magnetic interconnect other part 24f to the fourth magnetic interconnect one part 24e.

As shown in FIG. 12A, in the sensor 121, the first current circuit 71 supplies the first current I1 between the connection point CP5 of the first magnetic interconnect other part 21f and the second magnetic interconnect one part 22e, and the connection point CP6 of the third magnetic interconnect other part 23f and the fourth magnetic interconnect one part 24e.

Figure 12B:
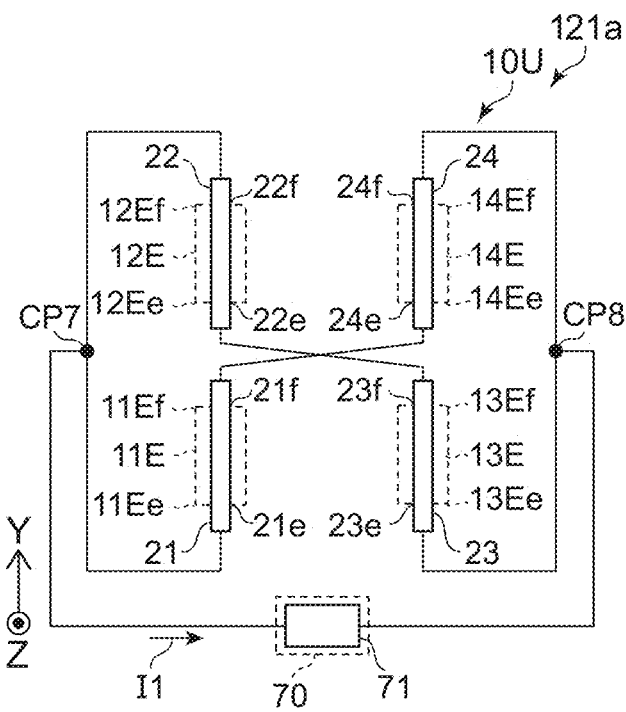
Figure 12C:
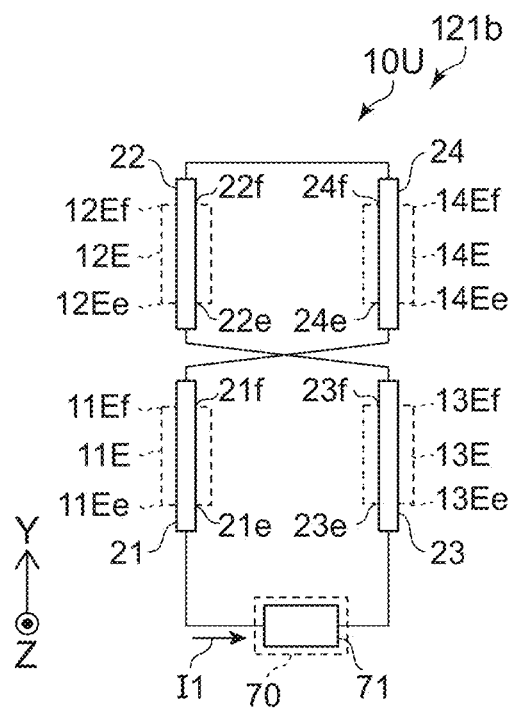
Figure 12D:
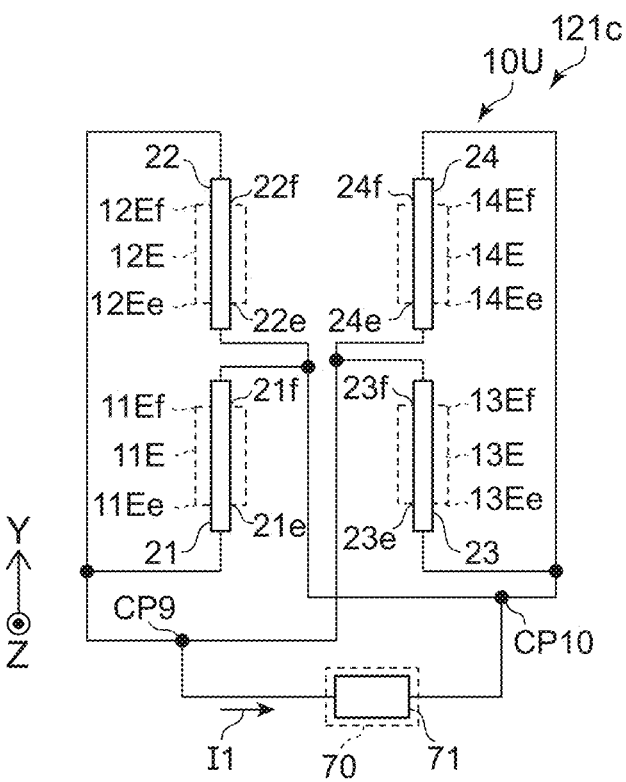

As shown in FIGS. 12B to 12D, in the sensors 121a to 121c, the configurations of the first to fourth magnetic elements 11E to 14E are the same as those in the sensor 121.

As shown in FIG. 12B, in the sensor 121a, the first current circuit 71 supplies the first current I1 between a connection point CP7 of the first magnetic interconnect one part 21e and the second magnetic interconnect other part 22f, and a connection point CP8 of the third magnetic interconnect one part 23e and the fourth magnetic interconnect other part 24f. In the sensor 112a, the first magnetic interconnect other part 21f is electrically connected to the fourth magnetic interconnect one part 24e. The second magnetic interconnect one part 22e is electrically connected to the third magnetic interconnect other part 23f.

As shown in FIG. 12C, in the sensor 121b, the first current circuit 71 supplies the first current I1 between the first magnetic interconnect one part 21e and the third magnetic interconnect one part 23e. In the sensor 112b, the first magnetic interconnect other part 21f is electrically connected to the fourth magnetic interconnect one part 24e. The second magnetic interconnect one part 22e is electrically connected to the third magnetic interconnect other part 23f. The second magnetic interconnect other part 22f is electrically connected to the fourth magnetic interconnect other part 24f.

As shown in FIG. 12D, in the sensor 121c, the first current circuit 71 supplies the first current I1 between a connection point CP9 of the first magnetic interconnect one part 21e, the second magnetic interconnect other part 22f, the third magnetic interconnect other part 23f, and the fourth magnetic interconnect one part 24e, and a connection point CP10 of the first magnetic interconnect other part 21f, the second magnetic interconnect one part 22e, the third magnetic interconnect one part 23e, and the fourth magnetic interconnect other part 24f.

Figure 13A:
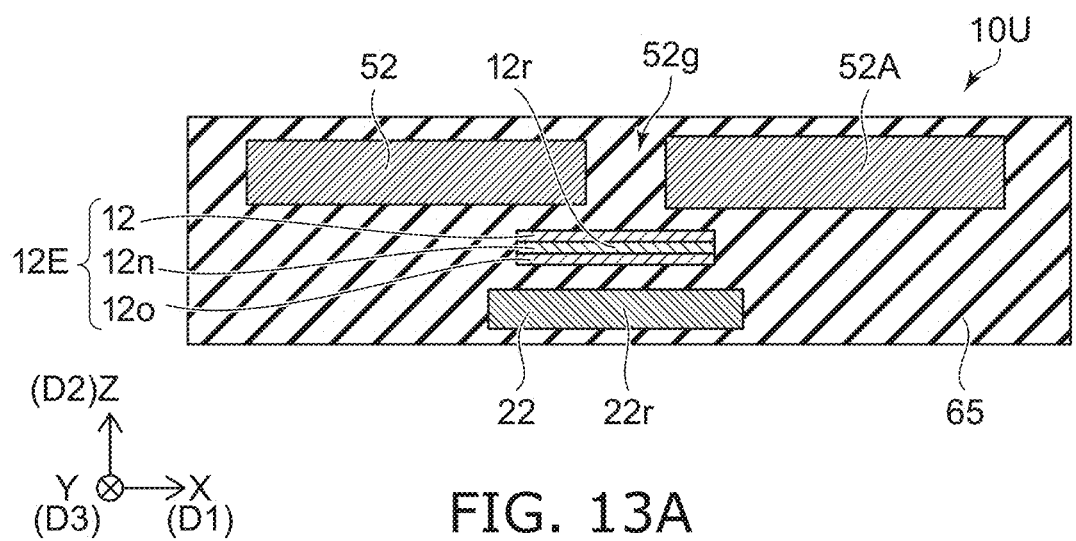
FIGS. 13A to 13C are schematic cross-sectional views illustrating the sensor according to the first embodiment.
Figure 13B:
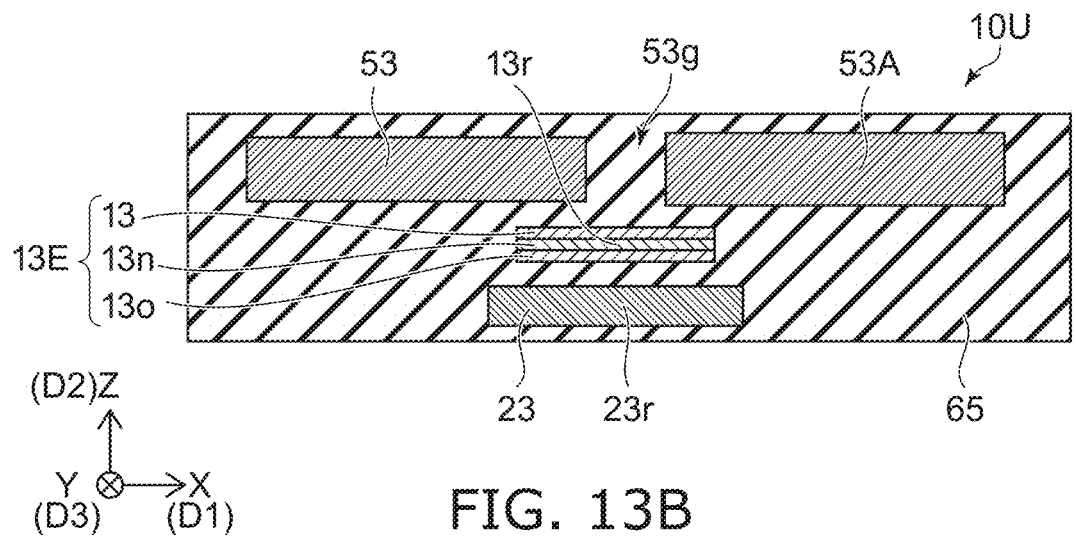
Figure 13C:
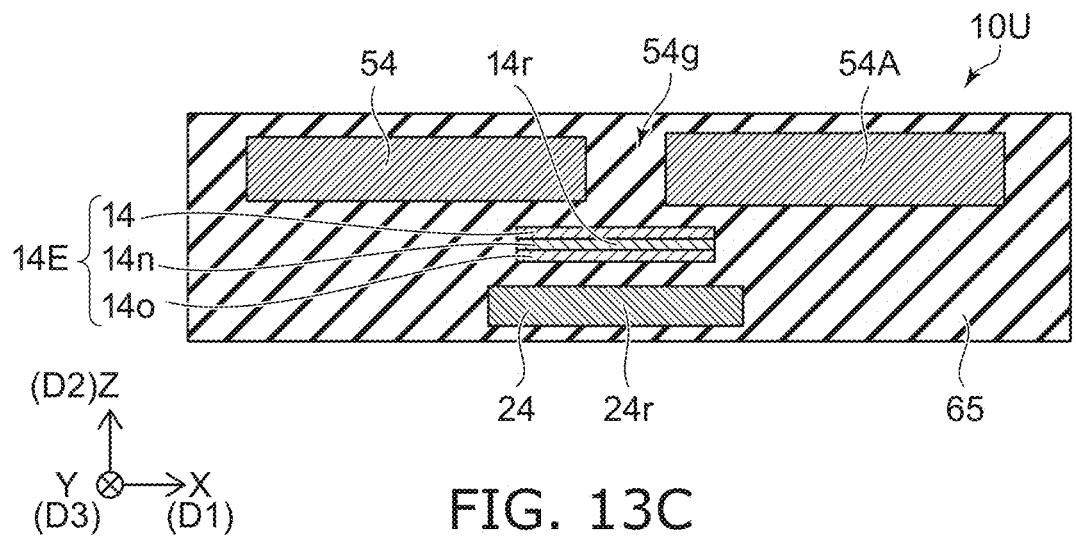

FIGS. 13A to 13C are schematic cross-sectional views illustrating the sensor according to the first embodiment.

As shown in FIG. 13A, the element part 10U includes a second magnetic member 52, a second counter magnetic member 52A, the second magnetic element 12E, and the second magnetic interconnect 22. A direction from the second magnetic member 52 to the second opposing magnetic member 52A is along the first direction D1. A second gap 52 g is provided between the second magnetic member 52 and the second counter magnetic member 52A.

The second magnetic element 12E includes a second magnetic region 12r. A direction from the second magnetic region 12r to the second gap 52g is along the second direction D2. A direction from the second magnetic interconnect 22 to the second magnetic region 12r is along the second direction D2.

The second magnetic element 12E includes a second magnetic layer 12, a second counter magnetic layer 12o, and a second non-magnetic layer 12n. The second non-magnetic layer 12n is provided between the second magnetic layer 12 and the second counter magnetic layer 12o. A direction from the second opposed magnetic layer 12o to the second magnetic layer 12 is along the second direction D2.

As shown in FIG. 13B, the element part 10U includes a third magnetic member 53, a third counter magnetic member 53A, the third magnetic element 13E, and the third magnetic interconnect 23. A direction from the third magnetic member 53 to the third opposed magnetic member 53A is along the first direction D1. A third gap 53g is provided between the third magnetic member 53 and the third opposed magnetic member 53A.

The third magnetic element 13E includes a third magnetic region 13r. A direction from the third magnetic region 13r to the third gap 53g is along the second direction D2. A direction from the third magnetic interconnect 23 to the third magnetic region 13r is along the second direction D2.

The third magnetic element 13E includes a third magnetic layer 13, a third counter magnetic layer 13o, and a third non-magnetic layer 13n. The third non-magnetic layer 13n is provided between the third magnetic layer 13 and the third counter magnetic layer 13o. A direction from the third magnetic layer 13o to the third magnetic layer 13 is along the second direction D2.

As shown in FIG. 13C, the element part 10U includes a fourth magnetic member 54, a fourth counter magnetic member 54A, the fourth magnetic element 14E, and the fourth magnetic interconnect 24. A direction from the fourth magnetic member 54 to the fourth counter magnetic member 54A is along the first direction D1. A fourth gap 54g is provided between the fourth magnetic member 54 and the fourth counter magnetic member 54A.

The fourth magnetic element 14E includes a fourth magnetic region 14r, and a direction from the fourth magnetic region 14r to the fourth gap 54g is along the second direction D2.

The fourth magnetic element 14E includes a fourth magnetic layer 14, a fourth counter magnetic layer 14o, and a fourth non-magnetic layer 14n. The fourth non-magnetic layer 14n is provided between the fourth magnetic layer 14 and the fourth counter magnetic layer 14o. A direction from the fourth magnetic layer 14o to the fourth magnetic layer 14 is along the second direction D2.

The configurations and materials of the second to fourth magnetic elements 12E to 14E may be the same as the configurations and materials of the first magnetic elements 11E.

FIGS. 14A to 14D are schematic perspective views illustrating the sensor according to the first embodiment.

Figures 14A, 14B:
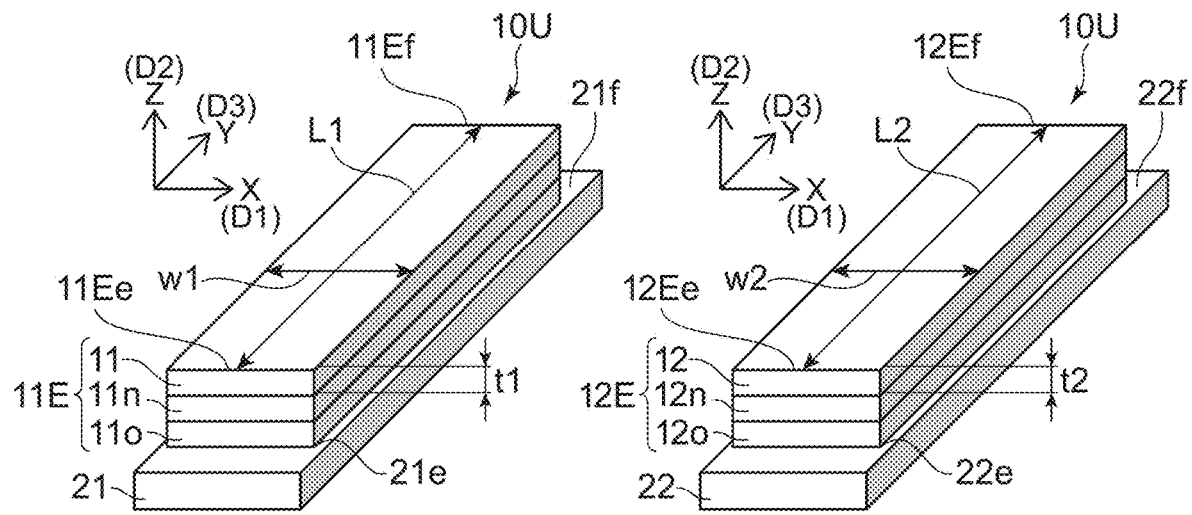
FIGS. 14A to 14D are schematic perspective views illustrating the sensor according to the first embodiment.

As shown in FIG. 14A, a length of the first magnetic layer 11 along the first direction D1 is defined as a length L1. A length of the first magnetic layer 11 along the third direction D3 is defined as a length w1. A length of the first magnetic layer 11 along the second direction D2 is defined as a length t1. The length L1 is longer than the length t1. The length w1 is, for example, longer than the length t1.

As shown in FIG. 14B, a length of the second magnetic layer 12 along the first direction D1 is defined as a length L2. A length of the second magnetic layer 12 along the third direction D3 is defined as a length w2. A length of the second magnetic layer 12 along the second direction D2 is defined as a length t2. The length L2 is longer than the length t2. The length w2 is, for example, longer than the length t2.

Figures 14C, 14D:
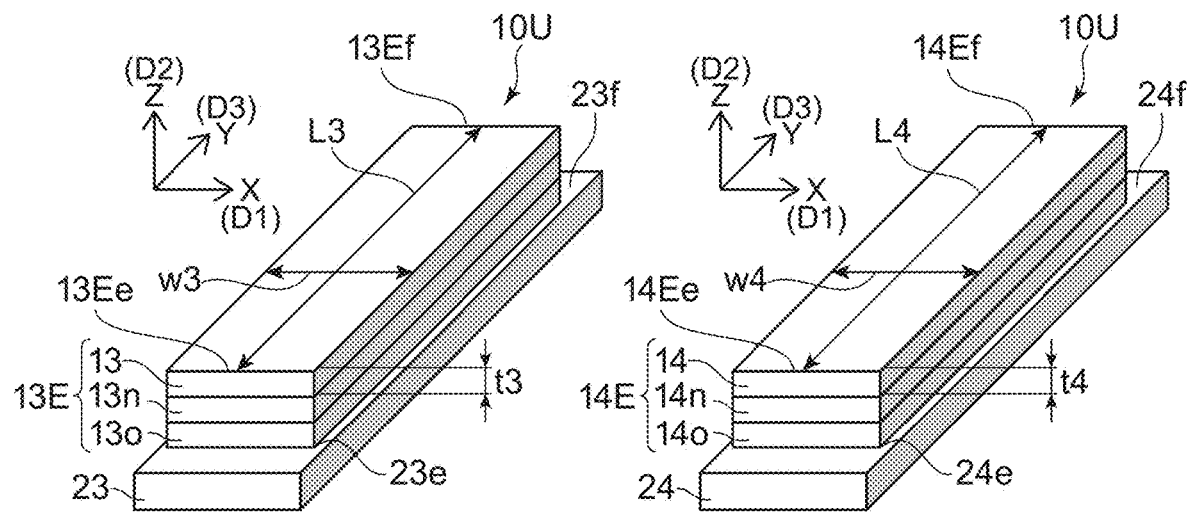

As shown in FIG. 14C, a length of the third magnetic layer 13 along the first direction D1 is defined as a length L3. A length of the third magnetic layer 13 along the third direction D3 is defined as a length w3. A length of the third magnetic layer 13 along the second direction D2 is defined as a length t3. The length L3 is longer than the length t3. The length w3 is, for example, longer than the length t3.

As shown in FIG. 14D, a length of the fourth magnetic layer 14 along the first direction D1 is defined as a length L4. A length of the fourth magnetic layer 14 along the third direction D3 is defined as a length w4. A length of the fourth magnetic layer 14 along the second direction D2 is defined as a length t4. The length L4 is longer than the length t4. The length w4 is, for example, longer than the length t4.

In the embodiment, each of the lengths L1 to L4 is, for example, not less than 0.1 μm and not more than 10 mm. Each of the lengths w1 to w4 is, for example, not less than 0.01 μm and not more than 1 mm. Each of the lengths t1 to t4 is, for example, not less than 1 nm and not more than 100 nm. It is easy to obtain good even function characteristics.

Second Embodiment

The second embodiment relates to an inspection device. As described later, the inspection device may include a diagnostic device.

Figure 15:
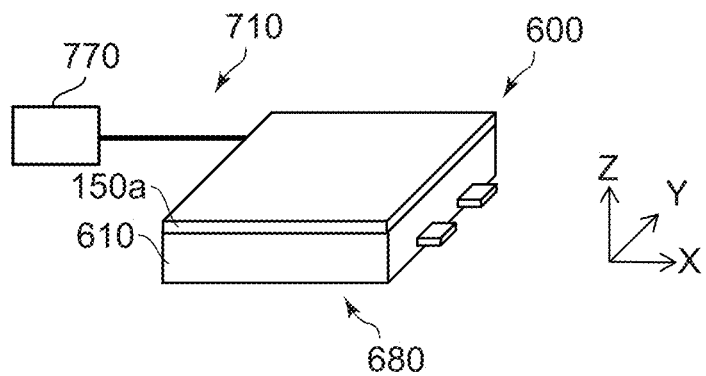
FIG. 15 is a schematic perspective view illustrating an inspection device according to a second embodiment.

FIG. 15 is a schematic perspective view illustrating an inspection device according to a second embodiment.

As shown in FIG. 15, an inspection device 710 according to the embodiment includes a sensor 150a and a processor 770. The sensor 150a may be the sensor according to any one of the first embodiments and a modification thereof. The processor 770 processes an output signal obtained from the sensor 150*a*. The processor 770 may compare the signal obtained from the sensor 150*a* with the reference value. The processor 770 can output the inspection result based on the processing result.

For example, the inspection device 710 inspects an inspection target 680. The inspection target 680 is, for example, an electronic device (including a semiconductor circuit or the like). The inspection target 680 may be, for example, a battery 610 or the like.

For example, the sensor 150*a* according to the embodiment may be used together with the battery 610. For example, a battery system 600 includes the battery 610 and the sensor 150*a*. The sensor 150*a* can detect the magnetic field generated by the current flowing through the battery 610.

Figure 16:
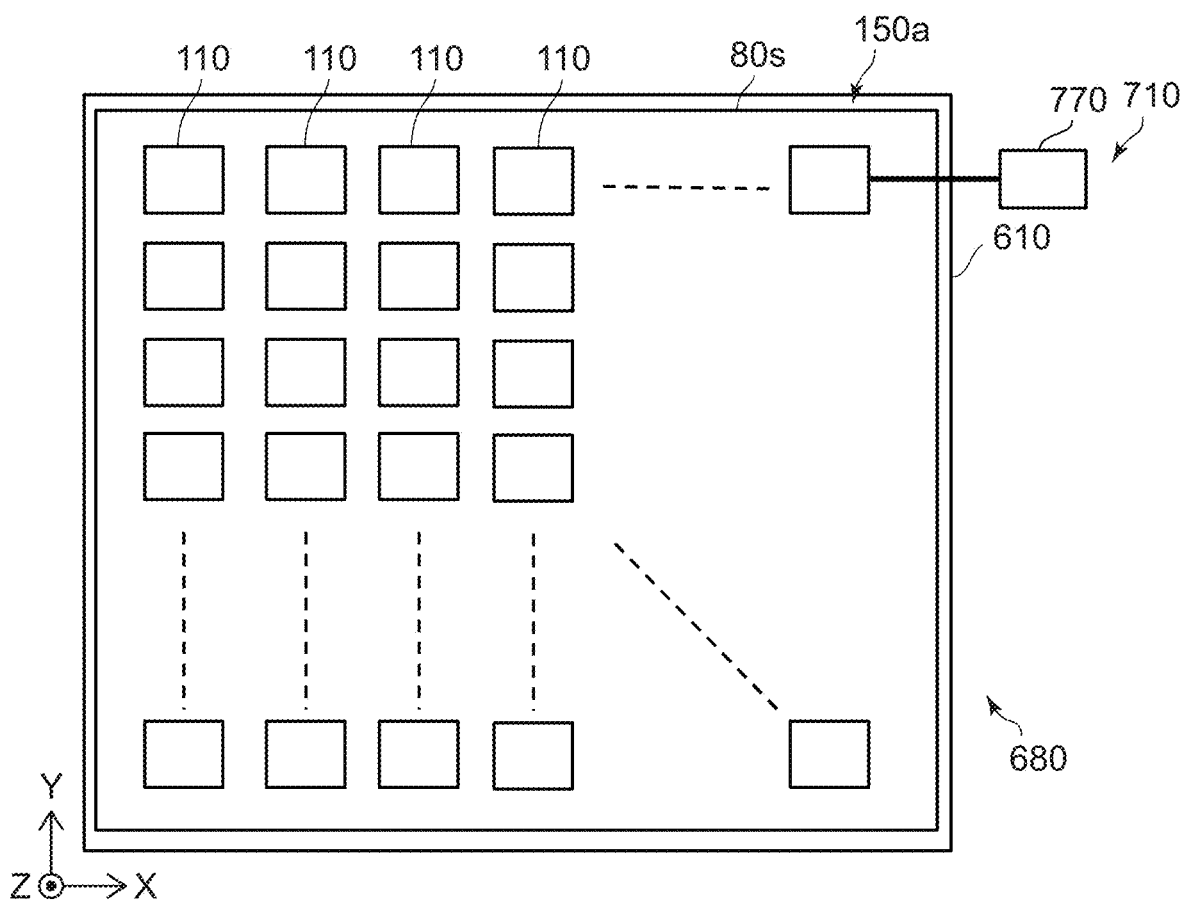
FIG. 16 is a schematic plan view illustrating the inspection device according to the second embodiment.

FIG. 16 is a schematic plan view illustrating the inspection device according to the second embodiment.

As shown in FIG. 16, the sensor 150*a* includes, for example, multiple sensors according to the embodiment. In this example, the sensor 150*a* includes multiple sensors (eg, sensor 110, etc.). The multiple sensors are arranged along, for example, two directions (for example, the X-axis direction and the Y-axis direction). The multiple sensors 110 are provided, for example, on a base body.

The sensor 150*a* can detect the magnetic field generated by the current flowing through the inspection target 680 (for example, the battery 610 may be used). For example, when the battery 610 approaches an abnormal state, an abnormal current may flow through the battery 610. By detecting the abnormal current with the sensor 150*a*, it is possible to know the change in the state of the battery 610. For example, in a state where the sensor 150*a* is placed close to the battery 610, the entire battery 610 can be inspected in a short time by using the sensor group driving means in two directions. The sensor 150*a* may be used for inspection of the battery 610 in manufacturing the battery 610.

The sensor according to the embodiment can be applied to, for example, the inspection device 710 such as a diagnostic device.

Figure 17:
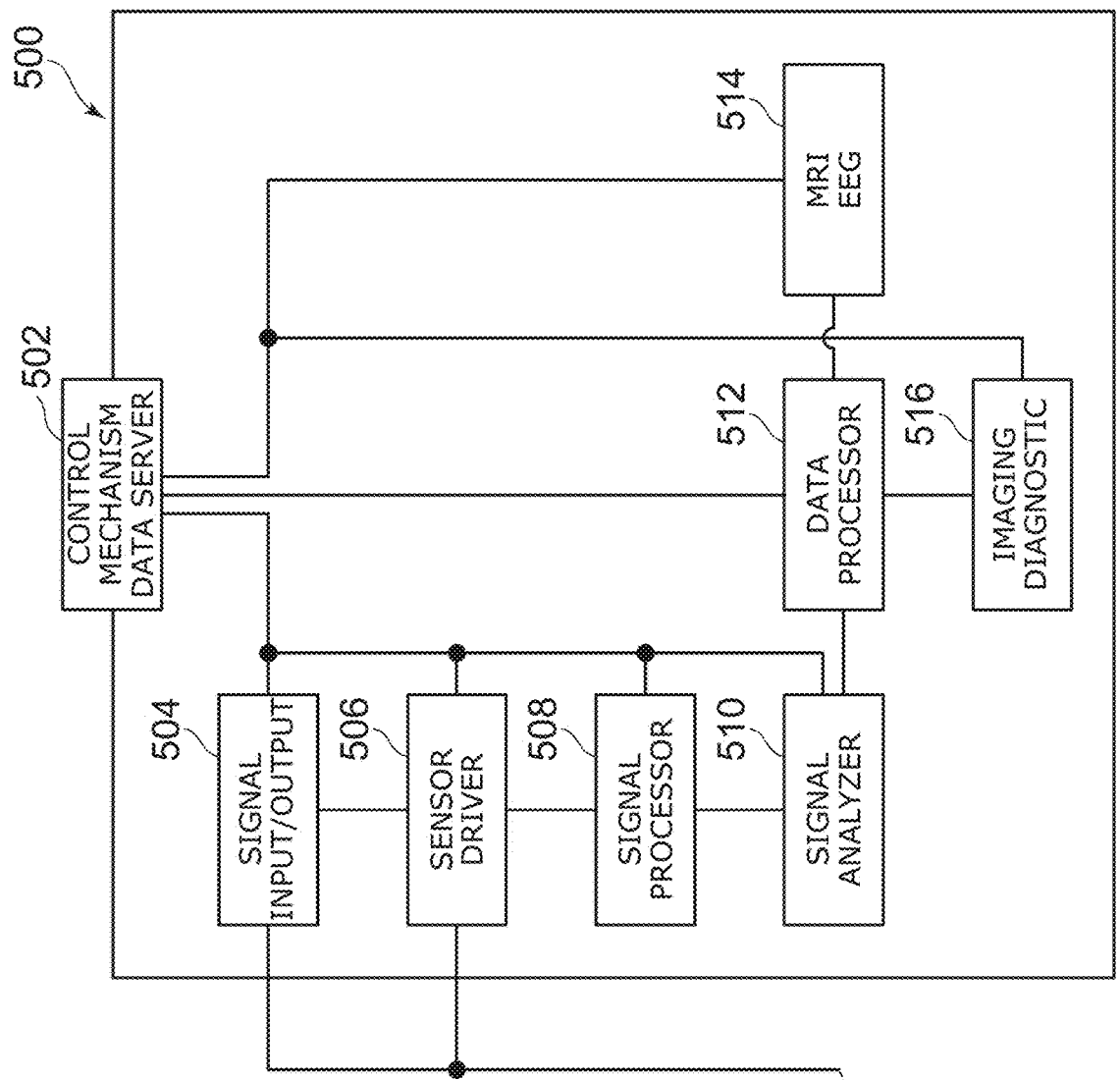
FIG. 17 is a schematic view illustrating the sensor and the inspection device according to the second embodiment.

FIG. 17 is a schematic view illustrating the sensor and the inspection device according to the second embodiment.

As shown in FIG. 17, a diagnostic device 500, which is an example of the inspection device 710, includes a sensor 150. The sensor 150 includes the sensors described with respect to the first embodiment and modifications thereof.

In the diagnostic apparatus 500, the sensor 150 is, for example, a magnetoencephalograph. The magnetoencephalograph detects the magnetic field generated by the cranial nerves. When the sensor 150 is used in a magnetoencephalograph, the size of the magnetic element included in the sensor 150 is, for example, not less than 1 mm and less than 10 mm.

As shown in FIG. 17, the sensor 150 (magnetoencephalogram) is attached to, for example, the head of a human body. The sensor 150 (magnetoencephalogram) includes a sensor part 301. The sensor 150 (magnetoencephalogram) may include multiple sensor parts 301. The number of the multiple sensor parts 301 is, for example, about 100 (for example, not less than 50 and not more than 150). The multiple sensor parts 301 are provided on a flexible base body 302.

The sensor 150 may include, for example, a circuit such as differential detection. The sensor 150 may include a sensor other than the sensor (for example, a potential terminal or an acceleration sensor).

A size of the sensor 150 is smaller than a size of a conventional SQUID (Superconducting Quantum Interference Device) sensor. Therefore, it is easy to install the multiple sensor parts 301. Installation of the multiple sensor parts 301 and other circuits is easy. The coexistence of the multiple sensor parts 301 and other sensors is easy.

The base body 302 may include an elastic body such as a silicone resin. For example, the multiple sensor parts 301 are provided to be connected to the base body 302. The base body 302 can be in close contact with the head, for example.

The input/output code 303 of the sensor part 301 is connected to a sensor driver 506 and a signal input/output 504 of the diagnostic device 500. The magnetic field measurement is performed in the sensor part 301 based on the electric power from the sensor driver 506 and the control signal from the signal input/output 504. The result is input to the signal input/output 504. The signal obtained by the signal input/output 504 is supplied to a signal processor 508. The signal processor 508 performs processing such as noise removal, filtering, amplification, and signal calculation. The signal processed by the signal processor 508 is supplied to a signal analyzer 510. The signal analyzer 510 extracts, for example, a specific signal for magnetoencephalography measurement. In the signal analyzer 510, for example, signal analysis for matching signal phases is performed.

The output of the signal analyzer 510 (data for which signal analysis has been completed) is supplied to a data processor 512. The data processor 512 performs data analysis. In this data analysis, for example, image data such as MRI (Magnetic Resonance Imaging) can be incorporated. In this data analysis, for example, scalp potential information such as EEG (Electroencephalogram) can be incorporated. For example, a data part 514 such as MRI or EEG is connected to the data processor 512. By the data analysis, for example, nerve ignition point analysis, inverse problem analysis, and the like are performed.

The result of the data analysis is supplied to, for example, an imaging diagnostic 516. Imaging is performed in the imaging diagnostic 516. Imaging assists in diagnosis.

The above series of operations is controlled by, for example, a control mechanism 502. For example, necessary data such as primary signal data or metadata in the middle of data processing is stored in the data server. The data server and the control mechanism may be integrated.

The diagnostic device 500 according to the embodiment includes the sensor 150 and the processor that processes an output signal obtained from the sensor 150. This processor includes, for example, at least one of a signal processor 508 and a data processor 512. The processor includes, for example, a computer.

In the sensor 150 shown in FIG. 17, the sensor part 301 is installed on the head of the human body. The sensor part 301 may be installed on the chest of the human body. This enables magnetocardiography measurement. For example, the sensor part 301 may be installed on the abdomen of a pregnant woman. This makes it possible to perform a fetal heartbeat test.

The sensor device including the subject is preferably installed in a shield room. Thereby, for example, the influence of geomagnetism or magnetic noise can be suppressed.

For example, a mechanism for locally shielding the measurement site of the human body or the sensor part 301 may be provided. For example, the sensor part 301 may be provided with a shield mechanism. For example, effective shielding may be performed in the signal analysis or the data processing.

In embodiments, the base body 302 may be flexible and may be substantially non-flexible. In the example shown in FIG. 17, the base body 302 is a continuous film processed into a hat shape. The base body 302 may be in a net shape. Thereby, for example, good wearability can be obtained. For example, the adhesion of the base body 302 to the human body is improved. The base body 302 may be helmet-shaped and may be rigid.

Figure 18:
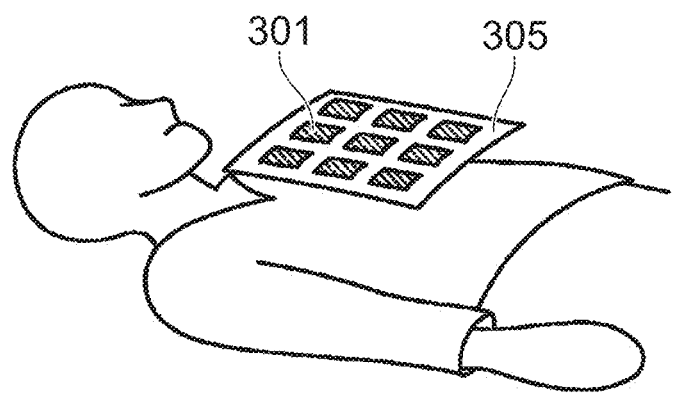
FIG. 18 is a schematic view illustrating the inspection device according to the second embodiment.

FIG. 18 is a schematic view illustrating the inspection device according to the second embodiment.

FIG. 18 is an example of a magnetocardiograph. In the example shown in FIG. 18, the sensor part 301 is provided on a flat plate-shaped hard base body 305.

In the example shown in FIG. 18, the input/output of the signal obtained from the sensor part 301 is the same as the input/output described with respect to FIG. 17. In the example shown in FIG. 18, the processing of the signal obtained from the sensor part 301 is the same as the processing described with respect to FIG. 17.

There is a reference example of using a SQUID (Superconducting Quantum Interference Device) sensor as a device for measuring a weak magnetic field such as a magnetic field generated from a living body. In this reference example, since superconductivity is used, the device is large and the power consumption is also large. The burden on the measurement target (patient) is heavy.

According to the embodiment, the device can be downsized. Power consumption can be suppressed. The burden on the measurement target (patient) can be reduced. According to the embodiment, the SN ratio of magnetic field detection can be improved. Sensitivity can be improved.

The embodiment may include the following configurations (eg, technical proposals).

Configuration 1
A sensor, comprising:
a first magnetic member;
a first counter magnetic member, a direction from the first magnetic member to the first counter magnetic member being along a first direction, a first gap being provided between the first magnetic member and the first counter magnetic member;
a first magnetic element including a first magnetic region, a second direction from the first magnetic region to the first gap crossing the first direction; and
a first magnetic interconnect, a direction from the first magnetic interconnect to the first magnetic region being along the second direction.

Configuration 2
The sensor according to Configuration 1, further comprising: a control circuit part including a first current circuit, and
the first current circuit is configured to supply a first current to the first magnetic interconnect, the first current including an AC component.

Configuration 3
The sensor according to Configuration 2, wherein
the first magnetic interconnect includes a first magnetic interconnect one part and a first magnetic interconnect other part,
a third direction from the first magnetic interconnect one part to the first magnetic interconnect other part crosses a plane including the first direction and the second direction, and
the first current flows in an orientation from the first magnetic interconnect one part to the first magnetic interconnect other part, or in an orientation from the first magnetic interconnect other part to the first magnetic interconnect one part.

Configuration 4
The sensor according to Configuration 2 or 3, wherein
the first current is supplied to the first magnetic interconnect,
an electrical resistance of the first magnetic element is a first resistance value when the first current is a first value current, the electrical resistance is a second resistance value when the first current is a second value current, and the electrical resistance is a third resistance value when the first current is a third value current,
an orientation of the second value current is opposite to an orientation of the third value current,
an absolute value of the first value current is smaller than an absolute value of the second value current, and smaller than an absolute value of the third value current, and
the first resistance value is lower than the second resistance value and the third resistance value, or higher than the second resistance value and the third resistance value.

Configuration 5
The sensor according to Configuration 2 or 3, wherein
an electrical resistance of the first magnetic element has characteristics of an even function with respect to the first current when the first current is supplied to the first magnetic interconnect.

Configuration 6
The sensor according to any one of Configurations 1 to 5, wherein
the first magnetic interconnect includes a first surface and a second surface,
a position of the second surface in the second direction is between a position of the first surface in the second direction and a position of the first magnetic member in the second direction, and
at least a part of the first surface is non-parallel to at least a part of the second surface.

Configuration 7
The sensor according to any one of Configurations 1 to 5, wherein
the first magnetic interconnect includes a first partial region and a second partial region,
a direction from the first partial region to the second partial region is along the first direction, and
a first thickness of the first partial region along the second direction is different from a second thickness of the second partial region along the second direction.

Configuration 8
The sensor according to any one of Configurations 1 to 5, wherein
the first magnetic interconnect includes a first partial region and a second partial region,
a direction from the first partial region to the second partial region is along the first direction, and
a material of at least a part of the first partial region is different from a material of at least a part of the second partial region.

Configuration 9
The sensor according to Configuration 3, wherein the control circuit part further includes an element circuit configured to supply an element current to the first magnetic element,
the first magnetic element includes a first magnetic element one end part and a first magnetic element other end part,
the first magnetic interconnect one part corresponds to the first magnetic element one end part,
the first magnetic interconnect other part corresponds to the first magnetic element other end part, and

19 the first element current flows from the first magnetic element one end part to the first magnetic element other end part.

Configuration 10

The sensor according to Configuration 1 or 2, wherein the element part further includes
- a second magnetic element including a second magnetic element one end part and a second magnetic element other end part,
- a first resistance element including a first resistance element one end part and a first resistance element other end part, and
- a second resistance element including a second resistance element one end part and a second resistance element other end part, the first magnetic element includes a first magnetic element one end part and a first magnetic element other end part, the first magnetic element one end part is electrically connected to the first resistance element one end part, the second magnetic element one end part is electrically connected to the first magnetic element other end part, the second resistance element one end part is electrically connected to the first resistance element other end part, the second magnetic element other end part is electrically connected to the second resistance element other end part, the first current circuit is configured to supply the first current to the second magnetic interconnect, the control circuit part further includes a detection circuit, and the detection circuit is configured to detect a change in potential between the first magnetic element other end part and the first resistance element other end part.

Configuration 11

The sensor according to Configuration 10, wherein the control circuit part further includes an element circuit, and the element circuit is configured to supply an element current between a connection point of the first magnetic element one end part and the first resistance element one end part, and a connection point of the second magnetic element other end part and the second resistance element other end part.

Configuration 12

The sensor according to Configuration 10 or 11, wherein the element part further includes a second magnetic interconnect, the first magnetic interconnect includes
- a first magnetic interconnect one part corresponding to the first magnetic element one end part, and
- a first magnetic interconnect other part corresponding to the first magnetic element other end part, the second magnetic interconnect includes
- a second magnetic interconnect one part corresponding to the second magnetic element one end part, and
- a second magnetic interconnect other part corresponding to the second magnetic element other end part, and when the first current flows in an orientation from the first magnetic interconnect other part to the first magnetic interconnect one part, the first current flows in an orientation from the second magnetic interconnect one part to the second magnetic interconnect other part.

20

Configuration 13

The sensor according to Configuration 1 or 2, wherein the element part further includes
- a second magnetic element including a second magnetic element one end part and a second magnetic element other end part,
- a third magnetic element including a third magnetic element one end part and a third magnetic element other end part, and
- a fourth magnetic element including a fourth magnetic element one end part and a fourth magnetic element other end part, the first magnetic element includes a first magnetic element one end part and the first magnetic element other end part, the first magnetic element one end part is electrically connected to the third magnetic element one end part, the second magnetic element one end part is electrically connected to the first magnetic element other end part, the fourth magnetic element one end part is electrically connected to the third magnetic element other end part, the second magnetic element other end part is electrically connected to the fourth magnetic element other end part, the first current circuit is configured to supply the first current to the second magnetic interconnect, the third magnetic interconnect and the fourth magnetic interconnect, the control circuit part further includes a detection circuit, and the detection circuit is configured to detect a change in potential between the first magnetic element other end part and the third magnetic element other end part.

Configuration 14

The sensor according to Configuration 13, wherein the control circuit part further includes an element circuit, and the element circuit is configured to supply an element current between a connection point of the first magnetic element one end part and the third magnetic element one end part, and a connection point of the second magnetic element other end part and the fourth magnetic element one other end part.

Configuration 15

The sensor according to Configuration 13 or 14, wherein the element part further includes a second magnetic interconnect, a third magnetic interconnect, and a fourth magnetic interconnect, the first magnetic interconnect includes
- a first magnetic interconnect one part corresponding to the first magnetic element one end part, and
- a first magnetic interconnect other part corresponding to the first magnetic element other end part, the second magnetic interconnect includes
- a second magnetic interconnect one part corresponding to the second magnetic element one end part, and
- a second magnetic interconnect other part corresponding to the second magnetic element other end part, the third magnetic interconnect includes
- a third magnetic interconnect one part corresponding to the third magnetic element one end part, and
- a third magnetic interconnect other part corresponding to the third magnetic element other end part, the fourth magnetic interconnect includes
- a fourth magnetic interconnect one part corresponding to the third magnetic element one end part, and
- a fourth magnetic interconnect other part corresponding to the fourth magnetic element other end part, and when the first current flows in an orientation from the first magnetic interconnect other part to the first magnetic interconnect one part, the first current flows in an orientation from the second magnetic interconnect one part to the second magnetic interconnect other part, the first current flows in an orientation from the third magnetic interconnect one part to the third magnetic interconnect other part, and the first current flows in an orientation from the fourth magnetic interconnect other part to the fourth magnetic interconnect one part.

Configuration 16

The sensor according to any one of Configurations 1 to 15, wherein
the first magnetic element includes
a first magnetic layer,
a first counter magnetic layer, and
a first non-magnetic layer provided between the first magnetic layer and the first counter magnetic layer, and
a direction from the first counter magnetic layer to the first magnetic layer is along the second direction.

Configuration 17

The sensor according to any one of Configurations 1 to 16, wherein
a position of the first magnetic element in the second direction is between a position of the first magnetic interconnect in the second direction and a position of the first magnetic member in the second direction.

Configuration 18

The sensor according to any one of Configurations 1 to 17, wherein
a part of the first magnetic element overlaps the first magnetic member in the second direction, and
an other part of the first magnetic element overlaps the first counter magnetic member in the second direction.

Configuration 19

The sensor according to any one of Configurations 1 to 18, wherein
the first magnetic element does not overlap the first magnetic member and the first counter magnetic member in the second direction.

Configuration 20

An inspection device, comprising:
the sensor according to any one of Configurations 1 to 19; and
a processor configured to process a signal output from the sensor.

According to the embodiment, a sensor and an inspection device can be provided, in which characteristics are possible to be improved.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as element parts, magnetic interconnects, control circuits, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors, and inspection devices practicable by an appropriate design modification by one skilled in the art based on the sensors, and the inspection devices described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
a first magnetic member;
a first counter magnetic member, a direction from the first magnetic member to the first counter magnetic member being along a first direction, a first gap being provided between the first magnetic member and the first counter magnetic member;
a first magnetic element including a first magnetic region, a second direction from the first magnetic region to the first gap crossing the first direction; and
a first magnetic interconnect, a direction from the first magnetic interconnect to the first magnetic region being along the second direction,
wherein
the first magnetic interconnect includes a first surface and a second surface,
a position of the second surface in the second direction is between a position of the first surface in the second direction and a position of the first magnetic member in the second direction, and
at least a part of the first surface is non-parallel to at least a part of the second surface.

2. The sensor according to claim 1, wherein
the first magnetic element includes
a first magnetic layer,
a first counter magnetic layer, and
a first non-magnetic layer provided between the first magnetic layer and the first counter magnetic layer, and
a direction from the first counter magnetic layer to the first magnetic layer is along the second direction.

3. The sensor according to claim 1, wherein
a position of the first magnetic element in the second direction is between a position of the first magnetic interconnect in the second direction and a position of the first magnetic member in the second direction.

4. The sensor according to claim 1, wherein
a part of the first magnetic element overlaps the first magnetic member in the second direction, and
an other part of the first magnetic element overlaps the first counter magnetic member in the second direction.

5. The sensor according to claim 1, wherein
the first magnetic element does not overlap the first magnetic member and the first counter magnetic member in the second direction.

6. An inspection device, comprising:
the sensor according to claim 1; and
a processor configured to process a signal output from the sensor.

7. The sensor according to claim 1, further comprising: a control circuit part including a first current circuit, and
the first current circuit is configured to supply a first current to the first magnetic interconnect, the first current including an AC component.

8. The sensor according to claim 7, wherein
the first current is supplied to the first magnetic interconnect,
an electrical resistance of the first magnetic element is a first resistance value when the first current is a first value current, the electrical resistance is a second resistance value when the first current is a second value current, and the electrical resistance is a third resistance value when the first current is a third value current,
an orientation of the second value current is opposite to an orientation of the third value current,
an absolute value of the first value current is smaller than an absolute value of the second value current, and smaller than an absolute value of the third value current, and
the first resistance value is lower than the second resistance value and the third resistance value, or higher than the second resistance value and the third resistance value.

9. The sensor according to claim 7, wherein
an electrical resistance of the first magnetic element has characteristics of an even function with respect to the first current when the first current is supplied to the first magnetic interconnect.

10. The sensor according to claim 7, wherein
the first magnetic interconnect includes a first magnetic interconnect one part and a first magnetic interconnect other part,
a third direction from the first magnetic interconnect one part to the first magnetic interconnect other part crosses a plane including the first direction and the second direction, and
the first current flows in an orientation from the first magnetic interconnect one part to the first magnetic interconnect other part, or in an orientation from the first magnetic interconnect other part to the first magnetic interconnect one part.

11. The sensor according to claim 10, wherein
the control circuit part further includes an element circuit configured to supply an element current to the first magnetic element,
the first magnetic element includes a first magnetic element one end part and a first magnetic element other end part,
the first magnetic interconnect one part corresponds to the first magnetic element one end part,
the first magnetic interconnect other part corresponds to the first magnetic element other end part, and
the first element current flows from the first magnetic element one end part to the first magnetic element other end part.

12. The sensor according to claim 1, wherein
the element part further includes
a second magnetic element including a second magnetic element one end part and a second magnetic element other end part,
a first resistance element including a first resistance element one end part and a first resistance element other end part, and
a second resistance element including a second resistance element one end part and a second resistance element other end part,
the first magnetic element includes a first magnetic element one end part and a first magnetic element other end part,
the first magnetic element one end part is electrically connected to the first resistance element one end part,
the second magnetic element one end part is electrically connected to the first magnetic element other end part,
the second resistance element one end part is electrically connected to the first resistance element other end part,
the second magnetic element other end part is electrically connected to the second resistance element other end part,
the first current circuit is configured to supply the first current to the second magnetic interconnect,
the control circuit part further includes a detection circuit, and
the detection circuit is configured to detect a change in potential between the first magnetic element other end part and the first resistance element other end part.

13. The sensor according to claim 12, wherein
the control circuit part further includes an element circuit, and
the element circuit is configured to supply an element current between a connection point of the first magnetic element one end part and the first resistance element one end part, and a connection point of the second magnetic element other end part and the second resistance element other end part.

14. The sensor according to claim 12, wherein
the element part further includes a second magnetic interconnect,
the first magnetic interconnect includes
a first magnetic interconnect one part corresponding to the first magnetic element one end part, and
a first magnetic interconnect other part corresponding to the first magnetic element other end part,
the second magnetic interconnect includes
a second magnetic interconnect one part corresponding to the second magnetic element one end part, and
a second magnetic interconnect other part corresponding to the second magnetic element other end part, and
when the first current flows in an orientation from the first magnetic interconnect other part to the first magnetic interconnect one part, the first current flows in an orientation from the second magnetic interconnect one part to the second magnetic interconnect other part.

15. The sensor according to claim 1, wherein
the element part further includes
a second magnetic element including a second magnetic element one end part and a second magnetic element other end part,
a third magnetic element including a third magnetic element one end part and a third magnetic element other end part, and
a fourth magnetic element including a fourth magnetic element one end part and a fourth magnetic element other end part,
the first magnetic element includes a first magnetic element one end part and the first magnetic element other end part, the first magnetic element one end part is electrically connected to the third magnetic element one end part, the second magnetic element one end part is electrically connected to the first magnetic element other end part, the fourth magnetic element one end part is electrically connected to the third magnetic element other end part, the second magnetic element other end part is electrically connected to the fourth magnetic element other end part, the first current circuit is configured to supply the first current to the second magnetic interconnect, the third magnetic interconnect and the fourth magnetic interconnect, the control circuit part further includes a detection circuit, and the detection circuit is configured to detect a change in potential between the first magnetic element other end part and the third magnetic element other end part.

16. The sensor according to claim 15, wherein
the control circuit part further includes an element circuit, and
the element circuit is configured to supply an element current between a connection point of the first magnetic element one end part and the third magnetic element one end part, and a connection point of the second magnetic element other end part and the fourth magnetic element other end part.

17. The sensor according to claim 15, wherein
the element part further includes a second magnetic interconnect, a third magnetic interconnect, and a fourth magnetic interconnect,
the first magnetic interconnect includes
  a first magnetic interconnect one part corresponding to the first magnetic element one end part, and
  a first magnetic interconnect other part corresponding to the first magnetic element other end part,
the second magnetic interconnect includes
  a second magnetic interconnect one part corresponding to the second magnetic element one end part, and
  a second magnetic interconnect other part corresponding to the second magnetic element other end part,
the third magnetic interconnect includes
  a third magnetic interconnect one part corresponding to the third magnetic element one end part, and
  a third magnetic interconnect other part corresponding to the third magnetic element other end part,
the fourth magnetic interconnect includes
  a fourth magnetic interconnect one part corresponding to the third magnetic element one end part, and
  a fourth magnetic interconnect other part corresponding to the fourth magnetic element other end part, and
when the first current flows in an orientation from the first magnetic interconnect other part to the first magnetic interconnect one part, the first current flows in an orientation from the second magnetic interconnect one part to the second magnetic interconnect other part, the first current flows in an orientation from the third magnetic interconnect one part to the third magnetic interconnect other part, and the first current flows in an orientation from the fourth magnetic interconnect other part to the fourth magnetic interconnect one part.

18. A sensor, comprising:
a first magnetic member;
a first counter magnetic member, a direction from the first magnetic member to the first counter magnetic member being along a first direction, a first gap being provided between the first magnetic member and the first counter magnetic member;
a first magnetic element including a first magnetic region, a second direction from the first magnetic region to the first gap crossing the first direction; and
a first magnetic interconnect, a direction from the first magnetic interconnect to the first magnetic region being along the second direction,
wherein
  the first magnetic interconnect includes a first partial region and a second partial region,
  a direction from the first partial region to the second partial region is along the first direction, and
  a first thickness of the first partial region along the second direction is different from a second thickness of the second partial region along the second direction.

19. The sensor according to claim 18, wherein
the first magnetic element includes
  a first magnetic layer,
  a first counter magnetic layer, and
  a first non-magnetic layer provided between the first magnetic layer and the first counter magnetic layer, and
a direction from the first counter magnetic layer to the first magnetic layer is along the second direction.

20. A sensor, comprising:
a first magnetic member;
a first counter magnetic member, a direction from the first magnetic member to the first counter magnetic member being along a first direction, a first gap being provided between the first magnetic member and the first counter magnetic member;
a first magnetic element including a first magnetic region, a second direction from the first magnetic region to the first gap crossing the first direction; and
a first magnetic interconnect, a direction from the first magnetic interconnect to the first magnetic region being along the second direction,
wherein
  the first magnetic interconnect includes a first partial region and a second partial region,
  a direction from the first partial region to the second partial region is along the first direction, and
  a material of at least a part of the first partial region is different from a material of at least a part of the second partial region.

* * * * *